US009322481B2

United States Patent
Wenchell et al.

(10) Patent No.: US 9,322,481 B2
(45) Date of Patent: *Apr. 26, 2016

(54) ROTATING VALVE ASSEMBLY INCLUDING MULTI-LUMEN SPHERICAL VALVE

(71) Applicant: Covidien LP, Mansfield, MA (US)

(72) Inventors: Thomas Wenchell, Durham, CT (US); Michael Ross Kessell, Auckland (NZ); Paul Neville Adams, Auckland (NZ); Stephen Lyle Weir, San Francisco, CA (US); Henry Bolanos, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 130 days.

This patent is subject to a terminal disclaimer.

(21) Appl. No.: 14/183,591

(22) Filed: Feb. 19, 2014

(65) Prior Publication Data

US 2014/0231687 A1 Aug. 21, 2014

Related U.S. Application Data

(63) Continuation of application No. 12/685,865, filed on Jan. 12, 2010, now Pat. No. 8,663,170, which is a continuation-in-part of application No. 11/640,009, filed on Dec. 15, 2006, now Pat. No. 7,874,308, which (Continued)

(30) Foreign Application Priority Data

May 29, 2003 (NZ) .................................. 526158

(51) Int. Cl.
*F16K 5/06* (2006.01)
*A47G 19/22* (2006.01)

(Continued)

(52) U.S. Cl.
CPC .............. *F16K 5/06* (2013.01); *A47G 19/2266* (2013.01); *A61F 5/4405* (2013.01); *B60K 15/04* (2013.01);

(Continued)

(58) Field of Classification Search
CPC ... F16K 5/0407; F16K 5/0605; F16K 5/0642; F16K 5/0626; F16K 27/067; F16K 31/5284; F16K 31/52458; Y10T 137/6035
USPC ...................................... 137/315.18
See application file for complete search history.

(56) References Cited

U.S. PATENT DOCUMENTS

| 133,215 A | 11/1872 | Endicott |
| 2,120,510 A | 3/1937 | Rhoads |

(Continued)

FOREIGN PATENT DOCUMENTS

| EP | 0820813 A2 | 1/1998 |
| EP | 1433712 A1 | 6/2004 |

(Continued)

OTHER PUBLICATIONS

European Search Report EP 11250029.3 dated Sep. 26, 2013.

*Primary Examiner* — Matthew W Jellett

(57) ABSTRACT

A valve assembly includes a valve housing having an upper body portion and a lower body portion that define an internal chamber for accommodating a valve member. The housing has axially aligned inlet and outlet ports. The valve assembly includes a generally spherical valve member seated within the internal chamber that defines first and second bores. The first bore defines a first longitudinal axis and the second bore defines a second longitudinal axis offset relative to the first longitudinal axis. The valve member is mounted for movement between a first position and a second position. The valve assembly includes a camming mechanism for moving the valve member between the first position and the second position, including cam surfaces formed on the exterior surface of the valve member and a cam pin formed on the interior surface of the upper body portion of the housing.

18 Claims, 15 Drawing Sheets

Related U.S. Application Data is a continuation of application No. 10/856,011, filed on May 28, 2004, now Pat. No. 7,165,568.

(60) Provisional application No. 60/516,569, filed on Oct. 31, 2003.

(51) Int. Cl.
  *A61F 5/44* (2006.01)
  *B60K 15/04* (2006.01)
  *B65D 47/06* (2006.01)
  *B65D 47/26* (2006.01)
  *B65D 51/28* (2006.01)
  *B67D 7/02* (2010.01)
  *F16K 31/524* (2006.01)
  *F16K 31/528* (2006.01)
  *F16K 37/00* (2006.01)

(52) U.S. Cl.
  CPC ............ *B60K 15/0406* (2013.01); *B65D 47/06* (2013.01); *B65D 47/266* (2013.01); *B65D 51/28* (2013.01); *B67D 7/0294* (2013.01); *F16K 5/0647* (2013.01); *F16K 31/524* (2013.01); *F16K 31/5284* (2013.01); *F16K 31/52458* (2013.01); *F16K 37/0008* (2013.01); *Y10T 137/6035* (2015.04)

(56) References Cited

U.S. PATENT DOCUMENTS

| | | | |
|---|---|---|---|
| 2,495,015 A | 4/1947 | McGrath | |
| 3,386,461 A | 6/1968 | Fisher | |
| 3,397,712 A | 8/1968 | Boroson | |
| 3,690,521 A | 9/1972 | Middleton et al. | |
| 3,703,249 A | 11/1972 | Middleton | |
| 3,703,250 A | 11/1972 | Middleton | |
| 4,141,476 A | 2/1979 | Rech | |
| 4,212,321 A | 7/1980 | Hulsey | |
| 4,262,691 A | 4/1981 | Kacal | |
| 4,446,883 A * | 5/1984 | Paul, Jr. | 137/315.18 |
| 4,540,411 A | 9/1985 | Bodicky | |
| 4,634,098 A | 1/1987 | Varden | |
| 4,655,078 A | 4/1987 | Johnson | |
| 4,867,414 A | 9/1989 | Hubacek | |
| 4,971,227 A | 11/1990 | Knickerbocker et al. | |
| 5,242,151 A | 9/1993 | Boehm et al. | |
| 5,265,845 A | 11/1993 | Gilliam | |
| 5,308,039 A | 5/1994 | King | |
| 5,395,342 A | 3/1995 | Yoon | |
| 5,478,318 A | 12/1995 | Yoon | |
| 5,676,657 A | 10/1997 | Yoon | |
| 5,743,437 A | 4/1998 | Moore et al. | |
| 5,944,051 A | 8/1999 | Johnson | |
| 6,595,946 B1 | 7/2003 | Pasqualucci | |
| 6,615,760 B1 | 9/2003 | Wise et al. | |
| 6,695,285 B1 | 2/2004 | Hotton et al. | |
| 6,758,359 B2 | 7/2004 | Yurkewicz et al. | |
| 7,165,568 B2 | 1/2007 | Kessell et al. | |
| 8,663,170 B2 | 3/2014 | Wenchell et al. | |
| 2004/0256004 A1 | 12/2004 | Kessell et al. | |

FOREIGN PATENT DOCUMENTS

| | | |
|---|---|---|
| EP | 1439339 A1 | 7/2004 |
| WO | 9803410 A1 | 1/1998 |
| WO | 0229303 A1 | 4/2002 |
| WO | 2004106782 A2 | 12/2004 |

* cited by examiner

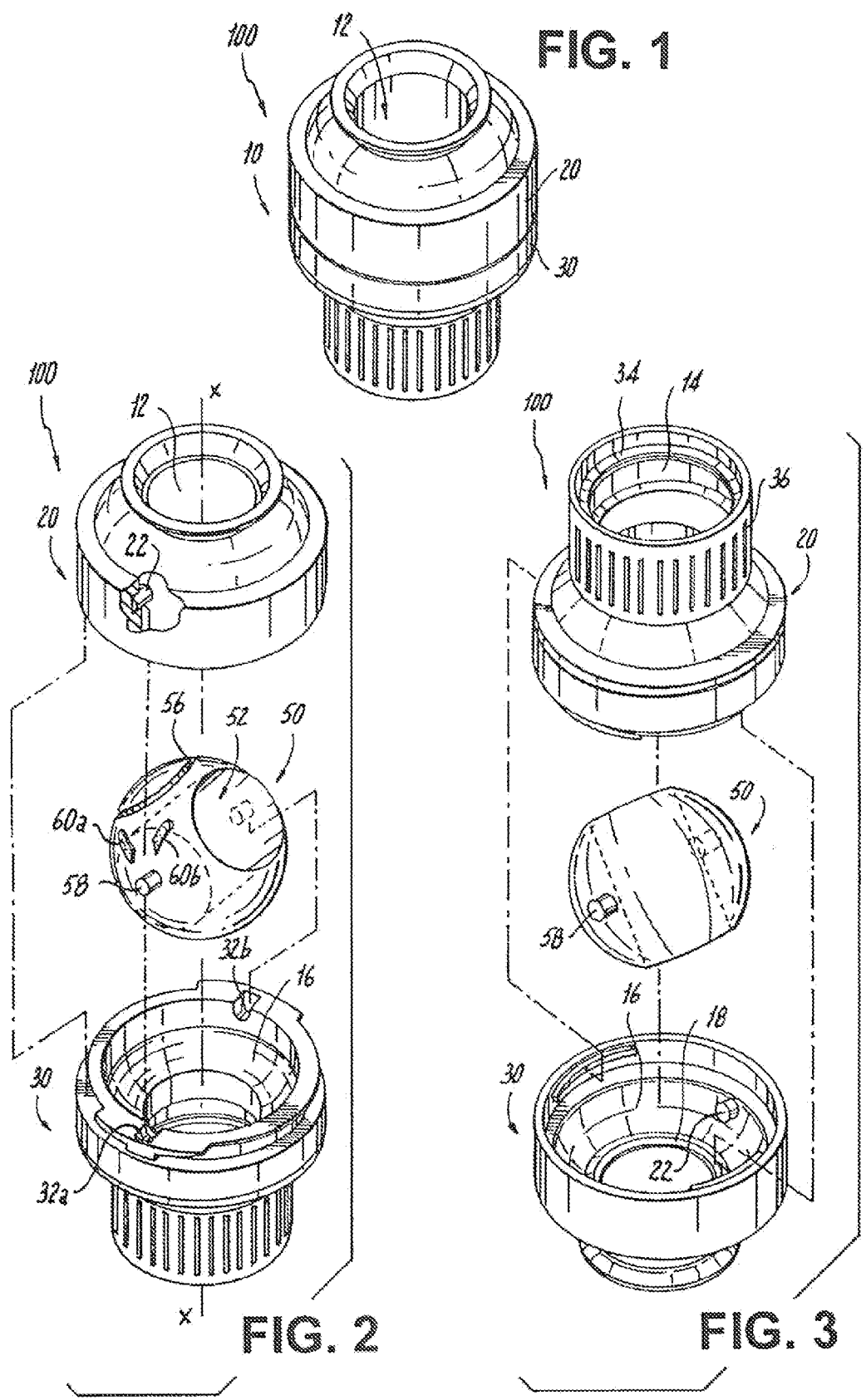

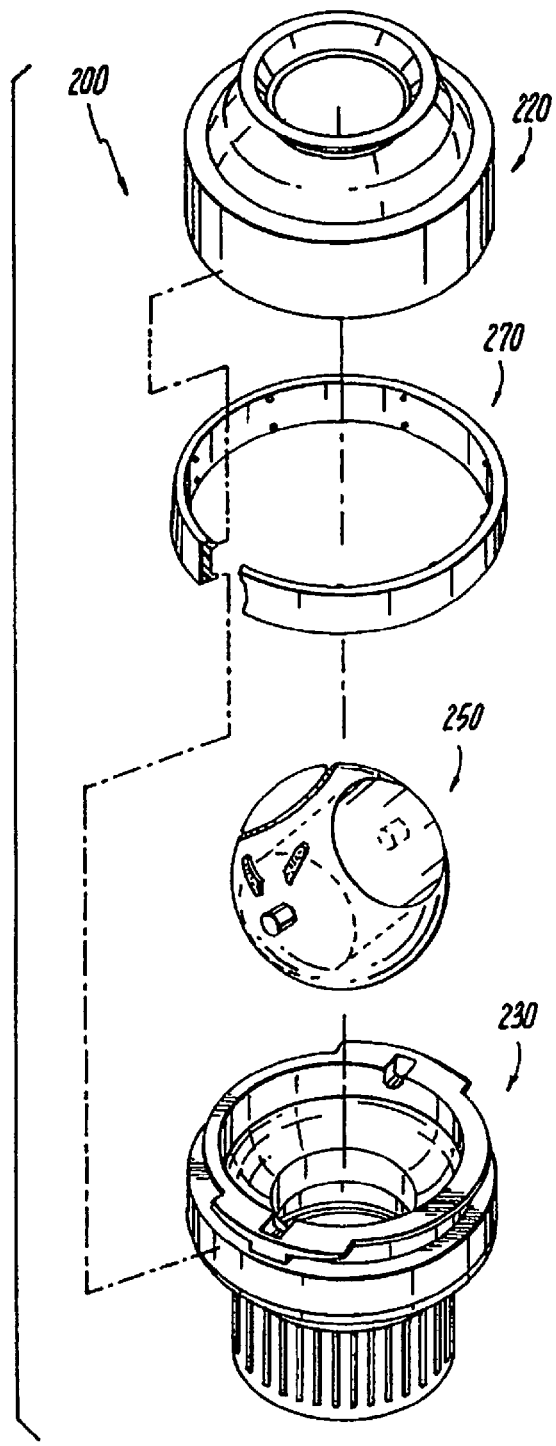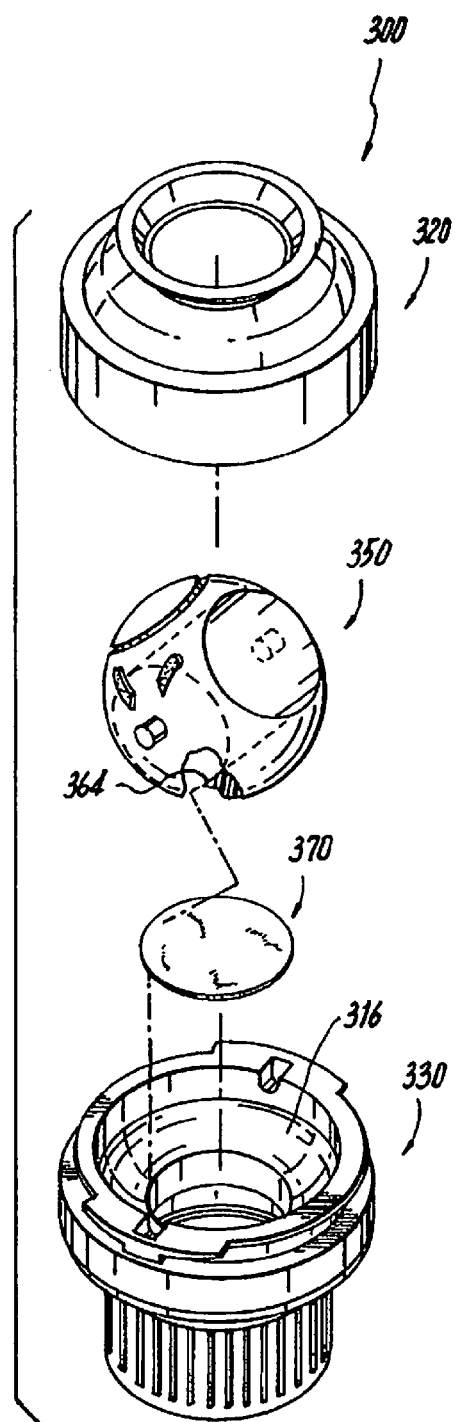
FIG. 4
FIG. 5

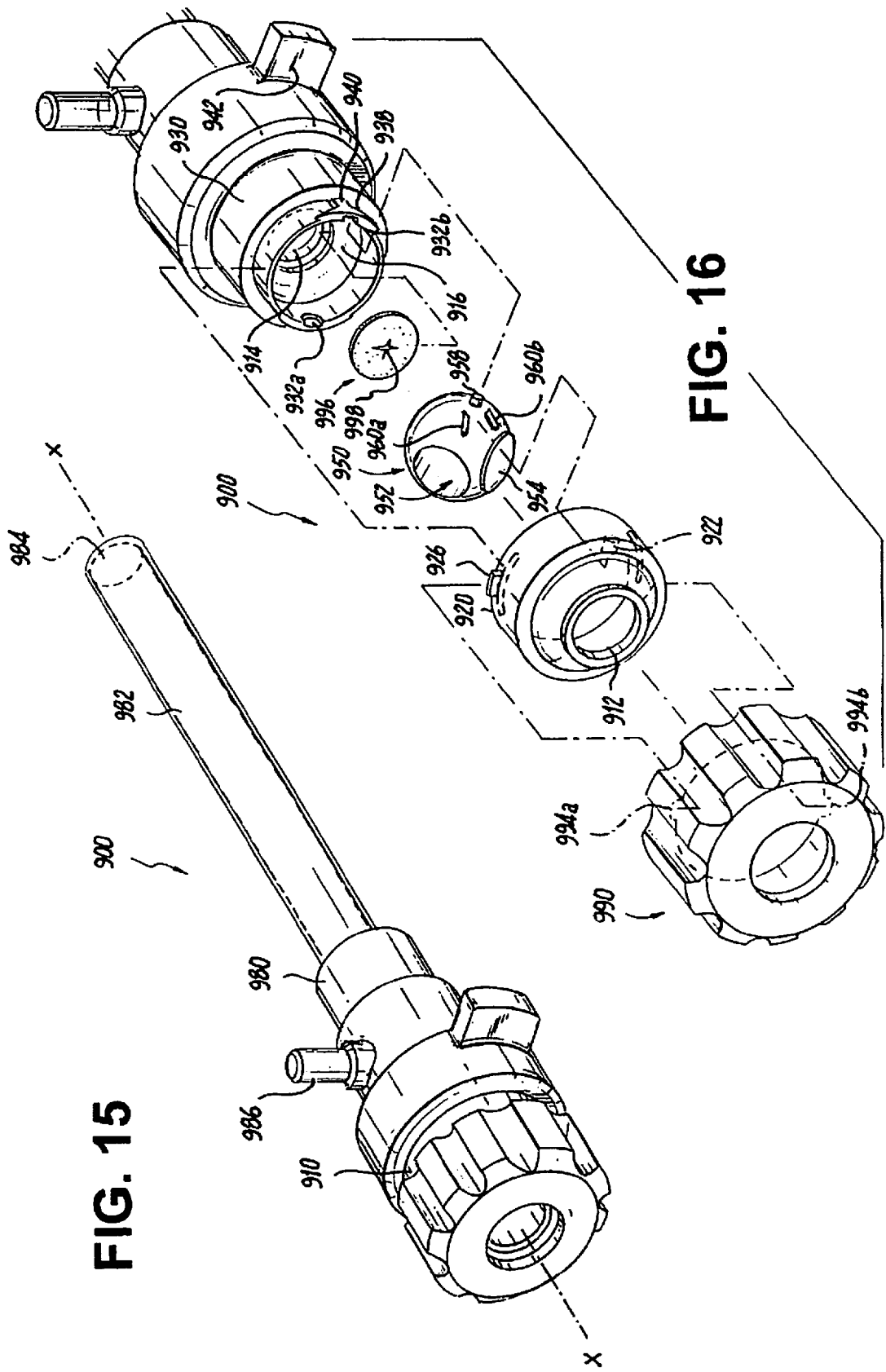

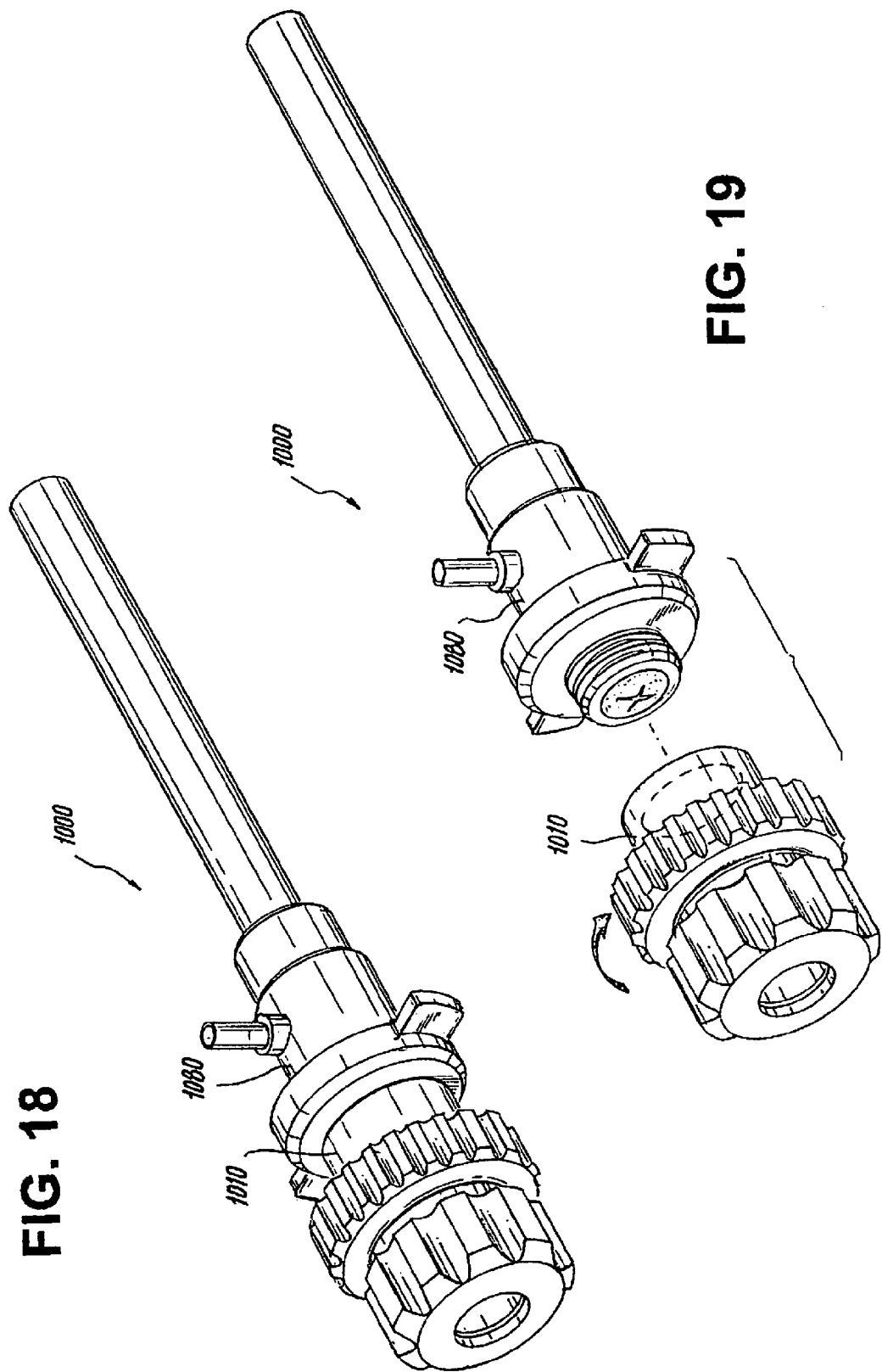

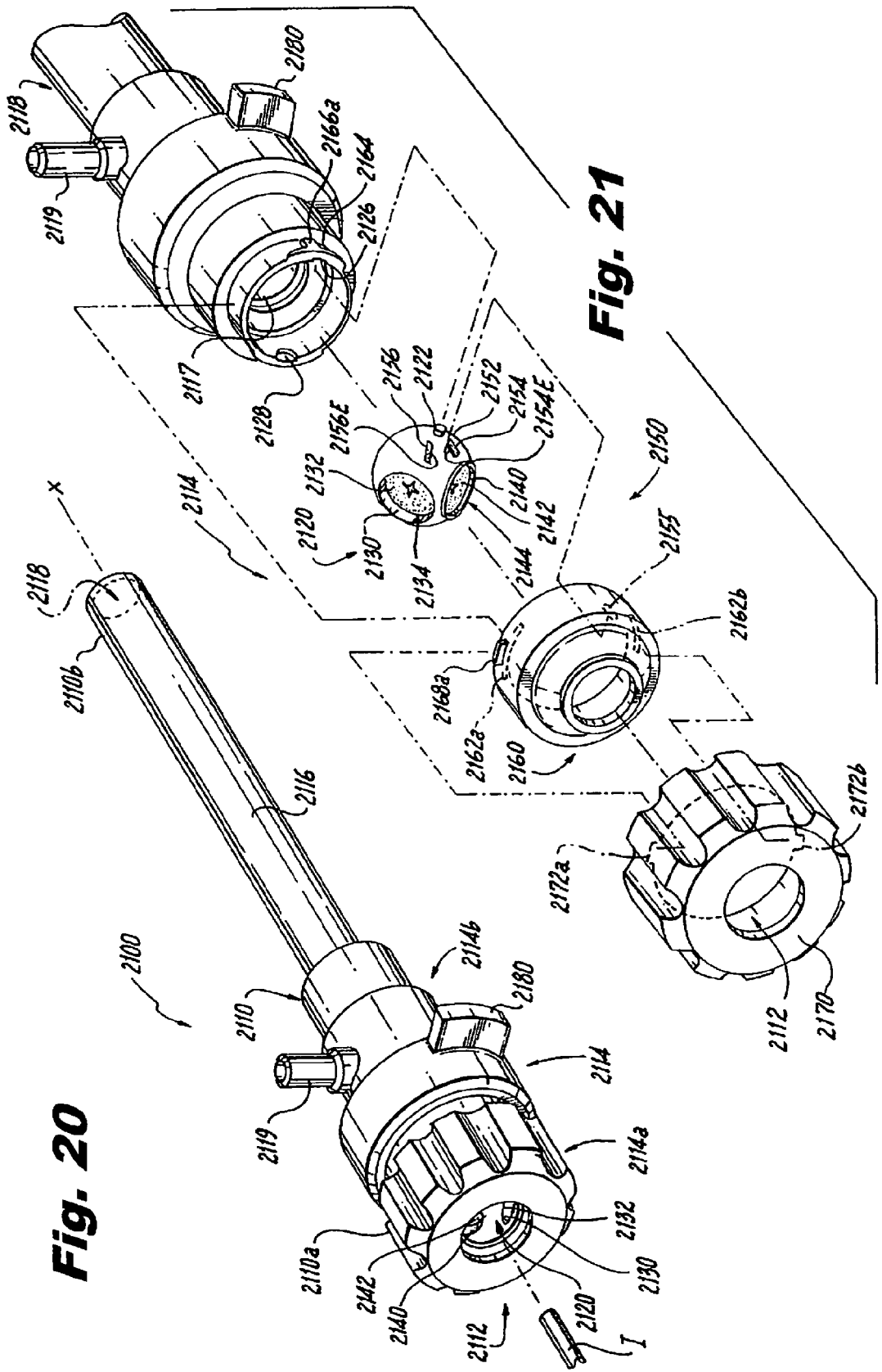

ROTATING VALVE ASSEMBLY INCLUDING MULTI-LUMEN SPHERICAL VALVE

CROSS REFERENCE TO RELATED APPLICATIONS

This application is a continuation of U.S. patent application Ser. No. 12/685,865, filed Jan. 12, 2010, which is a continuation-in-part of U.S. patent application Ser. No. 11/640,009, filed Dec. 15, 2006, now U.S. Pat. No. 7,874,308, which is a continuation of U.S. patent application Ser. No. 10/856,011, filed May 28, 2004, now U.S. Pat. No. 7,165,568, which claims the benefit of U.S. Provisional Patent Application Ser. No. 60/516,569, filed Oct. 31, 2003, and priority to New Zealand Provisional Patent Application Serial No. 526,158, filed May 29, 2003, the disclosures of each of these applications being herein incorporated by reference in their entirety.

TECHNICAL FIELD

The subject invention relates generally to the field of sealing mechanisms, and more particularly to, a compact valve assembly for use in a variety of applications, which includes a multi-lumen/bore, generally spherical valve member that is readily actuated between positions, e.g., open and closed positions, by a camming mechanism.

BACKGROUND

Ball valves are well known to those skilled in the art and are commonly used in a variety of applications and industries. Typically, in applications that concern controlling the flow of a fluid, an apertured ball valve is selected. In an apertured ball valve, a generally spherical valve member that has a flow aperture or passage formed therethrough is positioned for rotational movement within a valve housing. The valve operation or function is broken down into two separate stages. First, the ball moves between an open and a closed position by rotating through 90 degrees, such that the aperture or flow passage moves from an orientation coaxial with the flow direction, i.e. when the valve is open, to a position whereby the ball aperture is normal or perpendicular to the flow direction. Second, the valve seals in the closed position to prevent flow through the aperture across the ball valve. Therefore, the on-off control of flow through the valve is achieved by rotating the ball through 90 degrees within the valve housing.

In prior art ball valves; the rotation of the ball (i.e., valve member) is typically effectuated by an actuator mechanism that protrudes from the valve housing and is configured to rotate about an axis perpendicular to that of the valve flow. Such a valve is disclosed in U.S. Pat. No. 6,695,285 to Hotton et al.

Several disadvantages are associated with this type of ball valve. For example, the extension of an actuator from the sidewall of the valve is cumbersome and not desirable for applications where space limitations and physical access to the actuator are a concern. Still further, the actuator in these valves must be rotated or turned through at least 90 degrees in order for the valve to move between the fully open and fully closed positions.

Therefore, it would be beneficial therefore, to provide a valve/seal mechanism that is compact, reliable and readily actuated between the open and closed position and actuated with a minimal amount of rotational movement.

SUMMARY

The subject application is directed to a valve/seal assembly that is adapted for use in a variety of applications, such as for example, medical, consumer beverage, pharmaceutical containers, automobile, household appliance and marine. The disclosed valve includes, inter alia, a valve housing having an upper body portion and a lower body portion and a generally spherical valve member. The upper and lower body portions of the housing define an internal chamber for accommodating the valve member and a central axis for the valve. The housing also has axially aligned inlet and outlet ports formed in the upper and lower body portions, respectively.

The generally spherical valve member is seated within the internal chamber of the valve housing and has an axial bore extending therethrough. The valve member is mounted for movement between an open position; wherein the axial bore of the valve member is axially aligned with the inlet and outlet ports of the valve housing, and a closed position; wherein the axial bore of the valve member is out of alignment with the inlet and outlet ports of the valve housing. Preferably, the valve member moves between the open position and the closed position when the upper body portion of the housing is rotated about the central axis between about 57 degrees and about 77 degrees with respect to the lower body portion. It is presently envisioned that the valve member is mounted for axial rotation within the interior chamber about an axis extending perpendicular to the central axis defined by the upper and lower body portion of the valve housing.

Preferably, the valve member includes a sealing surface adapted for sealing engagement with a valve seat formed in the housing when the valve is in the closed position. In applications where a pressure is applied to the fluid or air metered by the valve, the sealing surface of the valve member is adapted to include an annular recess having an o-ring disposed therein.

The valve assembly further includes a mechanism that is operatively associated with the valve housing and the valve member for moving the valve member between the open position and the closed position when the upper body portion of the housing is rotated about the central axis with respect to the lower body portion. In a preferred embodiment, the mechanism for actuating the valve assembly is a camming mechanism.

In a present embodiment, the camming mechanism includes cam surfaces formed on the exterior surface of the valve member and a cam pin formed on the interior surface of the upper body portion of the housing. It is envisioned that the cam surfaces formed on the exterior surface of the valve member are defined by a pair of cam lobes formed at angles to one another. The cam lobes can be arcuate or linear in configuration.

In a further embodiment of the present invention, the camming mechanism includes at least one arcuate recess formed on the exterior surface of the valve member and a cam pin formed on the interior surface of the upper body portion of the housing for engaging with the cam recess.

In a preferred embodiment, the housing for the valve assembly includes means associated with the inlet port for engaging the valve with a receptacle or tubing. Additionally, if desired, the housing can includes means associated with the outlet port for engaging the valve with a receptacle or tubing.

In applications that require the valve to include a tamper-proof feature to ensure the purity of the substance contained within the bore of the valve member or in the receptacle or container, upon which the valve is affixed to, the valve further includes a frangible ring engaged with exterior of the valve housing to provide a visual indication of whether the valve has been opened. Alternatively or in combination, the valve can include a frangible sealing disc inserted into the interior chamber of the valve to again provide a visual indication of whether the valve has been opened. This sealing disc also functions as a secondary seal for the valve until its initial use. In this embodiment, it is envisioned that the valve member includes a mechanism for puncturing the disc when the valve is opened. For example, a sharp protuberance can be formed on the bottom of the valve member which cuts the sealing disc when the valve is moved from the closed to the open position.

In an alternative embodiment, the axial bore of the valve member is adapted and configured for receiving and storing an article of manufacture when the valve is in the closed position. For example, an award or small prize may be stored in the bore and revealed when the valve is opened. Still further, the valve could be mounted to a water bottle and the bore of the valve could contain a vitamin or supplement which is dropped into the water when the valve is opened.

It is further envisioned that the valve can include a mechanism associated with the valve housing for facilitating the axial rotation of the upper body portion of the housing relative to the lower body portion.

In an alternative embodiment, a plurality of flow passages are formed in the valve member and extend therethrough along an axis that is perpendicular to the axial bore such that when the valve is in the closed position, fluid or air traverses the valve through the plurality of flow passages.

The present disclosure is also directed to a surgical access device which includes, among other things, a valve housing, an elongated cannula sleeve operatively associated with the housing, a generally spherical valve member disposed within an interior chamber defined in the housing and a mechanism operatively associated with the valve housing and the valve member for moving the valve member between the open position and the closed position.

The valve housing defines an interior chamber and a valve seat for accommodating the valve member. Axially aligned inlet and outlet ports are formed in the housing and extend from the valve exterior to the interior chamber.

The elongated cannula sleeve that is operatively associated with the valve housing, has an elongated passageway extending therethrough that defines a longitudinal axis aligned with the inlet and outlet ports of the valve housing. In a disclosed embodiment, the cannula sleeve depends from a cannula housing associated with the valve housing. It is envisioned that the cannula housing can be detachably connected to the valve housing.

The generally spherical valve member is seated within the valve housing and has an axial bore extending therethrough. The valve member is mounted for movement between an open position and a closed position. In the open position, the axial bore of the valve member is axially aligned with the elongated passageway of the cannula sleeve and the inlet and outlet ports of the valve housing. In the closed position, the axial bore of the valve member extends perpendicular to the elongated passageway of the cannula sleeve and the inlet and outlet ports of the valve housing. It is envisioned that the valve member is mounted for axial rotation within the valve interior chamber about an axis extending perpendicular to the axially aligned inlet and outlet ports of the valve housing.

It is presently envisioned that the valve member includes a convex sealing surface, which is aligned with the inlet port of the valve housing when the valve member is in the closed position. In alternative embodiments that require a pressure tight seal, the sealing surface of the valve member includes an annular recess having an o-ring disposed therein.

In a preferred embodiment, the mechanism for moving the valve member includes cam surfaces formed on the exterior surface of the valve member and a cam pin mounted for movement relative to the cam surfaces of the valve member. Preferably, the cam pin extends radially inwardly from a drive ring supported on the valve housing and mounted for rotation about the longitudinal axis of the cannula sleeve. The rotation of the drive ring causes corresponding rotation of the valve member within the valve seat of the valve housing.

In a disclosed embodiment of the surgical access device, the cam surfaces formed on the exterior surface of the valve member are defined by a pair of cam lobes oriented with respect to the axis of rotation of the valve member at angles to one another.

In an alternative embodiment, the mechanism operatively associated with the valve housing and the valve member for moving the valve member between the open position and the closed position includes at least one arcuate recess formed on the exterior surface of the valve member and a cam pin formed on the interior surface of the housing for engaging with the cam recess.

It is presently preferred that the surgical access device further includes a membrane seal located proximal to the valve seat, the membrane seal having an opening axially aligned with the elongated passageway of the cannula sleeve. The opening is dimensioned to accommodate the passage of a surgical instrument therethrough.

Those skilled in the art would readily appreciate that the components of the disclosed valve assembly, or portions thereof, may be manufactured from any rigid, semi-rigid, hard or semi-hard material, such as plastic, rubber, metal or a composite. Still further, in medical applications the valve assembly can be made out of titanium or a similar biocompatible material.

Additionally, the generally spherical valve member can be formed to have an interference fit with the valve seat so as to provide a tighter seal. By forming the valve member or valve seat slightly out-of-round, a tighter seal is created and more force is required to open the valve.

It is also envisioned that a telescoping nozzle or sleeve can be disposed within the axial bore of the valve member and when the valve is moved to the open position, the nozzle or sleeve extends out of the valve inlet. This feature is useful in a variety of applications, such as for example, beverage or gasoline containers.

Still further, it is envisioned that the valve assembly of the present invention can be connected to stepper motor and thereby be operated remotely.

In accordance with various embodiments, the present invention may also provide for a valve assembly comprising: a) a valve housing having an upper body portion and a lower body portion, the upper and lower body portions defining an internal chamber for accommodating a valve member and a central axis for the valve, the housing having axially aligned inlet and outlet ports formed in the upper and lower body portions, respectively; b) a generally spherical valve member seated within the internal chamber of the valve housing and having first and second bores extending therethrough, the first bore defining a first longitudinal axis and the second bore having a second longitudinal axis offset relative to the first longitudinal axis, the valve member mounted for movement between a first position wherein the first bore of the valve member is axially aligned with the inlet and outlet ports of the valve housing and the second bore of the valve member is axially misaligned with the inlet and outlet ports of the valve housing, and a second position wherein the second bore of the valve member is axially aligned with the inlet and outlet ports of the valve housing and the first bore of the valve member is axially misaligned with the inlet and outlet ports of the valve housing; and c) a camming mechanism for moving the valve member between the first position and the second position, including cam surfaces formed on the exterior surface of the valve member and a cam pin formed on the interior surface of the upper body portion of the housing, wherein the cam surfaces formed on the exterior surface of the valve member are defined by a pair of arcuate cam lobes formed at angles to one another.

The first bore may define a first diameter and the second bore may define a second diameter, the first diameter being different from the second diameter. Each one of the first and second bores may be configured and dimensioned to receive, when aligned with the inlet and outlet ports of the valve housing, a surgical instrument. There may be disposed in each one of the first and second bores respective first and second seals. The first seal disposed in the first bore may be configured and dimensioned to sealingly engage with a surgical instrument having a first instrument diameter and the seal of the second bore may be configured and dimensioned to sealingly engage with a surgical instrument having a second instrument diameter that is different from the first instrument diameter. The valve member may be mounted for movement to a third position wherein the first and second bores of the valve member are both axially misaligned with the inlet and outlet ports of the valve housing. The camming mechanism may include at least one arcuate recess formed on the exterior surface of the valve member and a cam pin formed on the interior surface of the upper body portion of the housing for engaging with the cam recess. The valve member may be mounted for rotation within the interior chamber about an axis extending perpendicular to the central axis defined by the upper and lower body portion of the valve housing. The housing may include a connection for a cannula tube. The valve assembly may also include a rotation mechanism for facilitating the axial rotation of the lower body portion of the housing relative to the upper body portion. The valve member may move between the first position and the second position when the upper body portion of the housing is rotated about the central axis between about 57 degrees and about 77 degrees with respect to the lower body portion.

In accordance with various embodiments, the present invention may also provide for a surgical device comprising: a) a valve housing defining a valve seat for accommodating a valve member, and having axially aligned inlet and outlet ports; b) an elongated cannula sleeve operatively associated with the valve housing and having an elongated passageway extending therethrough which defines a longitudinal axis aligned with the inlet and outlet ports of the valve housing; c) a generally spherical valve member seated within the internal chamber of the valve housing and having first and second bores extending therethrough, the first bore defining a first longitudinal axis and the second bore having a second longitudinal axis offset relative to the first longitudinal axis, the valve member mounted for movement between a first position wherein the first bore of the valve member is axially aligned with the inlet and outlet ports of the valve housing and the second bore of the valve member is axially misaligned with the inlet and outlet ports of the valve housing, and a second position wherein the second bore of the valve member is axially aligned with the inlet and outlet ports of the valve housing and the first bore of the valve member is axially misaligned with the inlet and outlet ports of the valve housing; and d) a camming mechanism including cam surfaces formed on the exterior surface of the valve member and a cam pin mounted for movement relative to the cam surfaces of the valve member, wherein the cam pin extends radially inwardly from a drive ring supported on the valve housing and mounted for rotation about the longitudinal axis of the cannula sleeve, and wherein rotation of the drive ring causes corresponding rotation of the valve member within the valve seat of the valve housing, and wherein the cam surfaces formed on the exterior surface of the valve member are defined by a pair of cam lobes oriented with respect to the axis of rotation of the valve member at angles to one another.

The first bore may define a first diameter and the second bore may define a second diameter, the first diameter being different from the second diameter. Each one of the first and second bores may be configured and dimensioned to receive, when aligned with the inlet and outlet ports of the valve housing, a surgical instrument. There may be disposed in each one of the first and second bores respective first and second seals. The first seal disposed in the first bore may be configured and dimensioned to sealingly engage with a surgical instrument having a first instrument diameter and the seal of the second bore may be configured and dimensioned to sealingly engage with a surgical instrument having a second instrument diameter that is different from the first instrument diameter. The valve member may be mounted for movement to a third position wherein the first and second bores of the valve member are both axially misaligned with the inlet and outlet ports of the valve housing. The camming mechanism may include at least one arcuate recess formed on the exterior surface of the valve member and a cam pin formed on the interior surface of the upper body portion of the housing for engaging with the cam recess. The valve member may be mounted for rotation within the interior chamber about an axis extending perpendicular to the central axis defined by the upper and lower body portion of the valve housing. The surgical device may also include a rotation mechanism for facilitating the axial rotation of the lower body portion of the housing relative to the upper body portion. The valve member may move between the first position and the second position when the upper body portion of the housing is rotated about the central axis between about 57 degrees and about 77 degrees with respect to the lower body portion.

In accordance with various embodiments, the present invention may also provide for a valve assembly comprising: a) a valve housing defining a valve seat for accommodating a valve member, and having axially aligned inlet and outlet ports; b) a generally spherical valve member seated within the internal chamber of the valve housing and having first and second bores extending therethrough, the first bore defining a first longitudinal axis and the second bore having a second longitudinal axis offset relative to the first longitudinal axis, the valve member mounted for movement between a first position wherein the first bore of the valve member is axially aligned with the inlet and outlet ports of the valve housing and the second bore of the valve member is axially misaligned with the inlet and outlet ports of the valve housing, and a second position wherein the second bore of the valve member is axially aligned with the inlet and outlet ports of the valve housing and the first bore of the valve member is axially misaligned with the inlet and outlet ports of the valve housing, wherein the valve member is mounted for axial rotation within the valve seat about an axis extending perpendicular to the axially aligned inlet and outlet ports of the valve housing; and c) a camming mechanism operatively associated with the valve housing and the valve member for moving the valve member between the first position and the second position including cam surfaces formed on the exterior surface of the valve member and a cam pin mounted for movement relative to the cam surfaces of the valve member, wherein the cam surfaces formed on the exterior surface of the valve member are defined by a pair of cam lobes oriented with respect to the axis of rotation of the valve member at angles to one another.

The first bore may define a first diameter and the second bore may define a second diameter, the first diameter being different from the second diameter. Each one of the first and second bores may be configured and dimensioned to receive, when aligned with the inlet and outlet ports of the valve housing, a surgical instrument. There may be disposed in each one of the first and second bores respective first and second seals. The first seal disposed in the first bore may be configured and dimensioned to sealingly engage with a surgical instrument having a first instrument diameter and the seal of the second bore may be configured and dimensioned to sealingly engage with a surgical instrument having a second instrument diameter that is different from the first instrument diameter. The valve member may be mounted for movement to a third position wherein the first and second bores of the valve member are both axially misaligned with the inlet and outlet ports of the valve housing. The camming mechanism may include at least one arcuate recess formed on the exterior surface of the valve member and a cam pin formed on the interior surface of the upper body portion of the housing for engaging with the cam recess. The valve member may be mounted for rotation within the interior chamber about an axis extending perpendicular to the central axis defined by the upper and lower body portion of the valve housing. The housing may include a connection for a cannula tube. The valve assembly may also include a rotation mechanism for facilitating the axial rotation of the lower body portion of the housing relative to the upper body portion. The valve member may move between the first position and the second position when the upper body portion of the housing is rotated about the central axis between about 57 degrees and about 77 degrees with respect to the lower body portion. The cam pin may extends radially inwardly from a drive ring supported on the valve housing and may be mounted for axial rotation relative to the axially aligned inlet and outlet ports, wherein rotation of the drive ring causes corresponding rotation of the valve member within the valve seat of the valve housing.

BRIEF DESCRIPTION OF THE DRAWINGS

So that those having ordinary skill in the art to which the present application appertains will more readily understand how to make and use the surgical access device and valve assembly of the present invention, embodiments thereof will be described in detail hereinbelow with reference to the drawings, wherein:

FIG. 1 is a perspective view of a valve assembly constructed in accordance with a preferred embodiment of the subject invention;

FIG. 2 is an exploded perspective view from above of the valve assembly of FIG. 1 with parts separated for ease of illustration;

FIG. 3 is an exploded perspective view from below of the valve assembly of FIG. 1 with parts separated for ease of illustration;

FIG. 4 is an exploded perspective view of an alternative embodiment of the valve assembly of the present invention with parts separated for ease of illustration, wherein the valve includes a frangible ring;

FIG. 5 is an exploded perspective view of an alternative embodiment of the valve assembly of the present invention with parts separated for ease of illustration, wherein the valve includes a sealing disc disposed within the interior chamber of the housing;

FIG. 15 is a perspective view of a surgical access device constructed in accordance with a preferred embodiment of the subject invention;

FIG. 16 is an exploded perspective view of the surgical access device of FIG. 15 with parts separated for ease of illustration;

FIG. 18 is a perspective view of another embodiment of the surgical access device of the subject invention, which includes a detachable valve housing; and FIG. 19 is a perspective view of the surgical access device of FIG. 18, with the valve housing separated from the cannula housing for ease of illustration.

FIG. 20 is a perspective view of one embodiment of a surgical access device constructed in accordance with the present disclosure;

FIG. 21 is a perspective view, with parts separated, of a cannula housing of the surgical access device of FIG. 20;

Figure 3A:
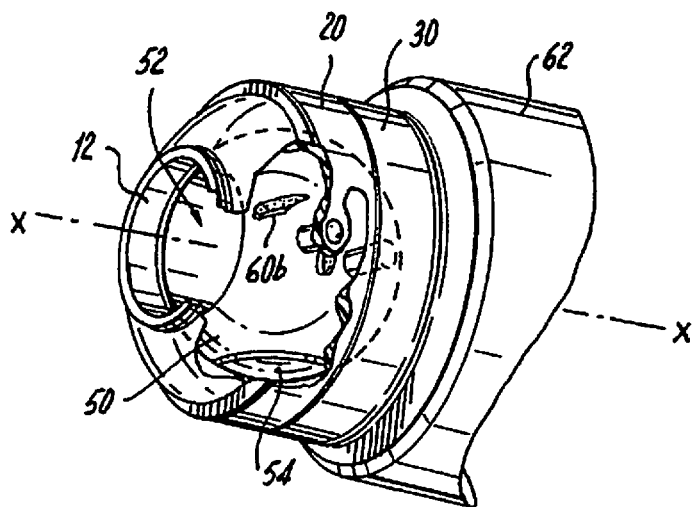
FIGS. 3a-3c are progressive views illustrating movement of the valve assembly of FIG. 1 between open, intermediate, and closed positions.

These and other features of the valve assembly and surgical access device of the present application will become more readily apparent to those having ordinary skill in the art form the following detailed description of the preferred embodiments.

DETAILED DESCRIPTION

Referring now to the drawings wherein like reference numerals identify similar structural elements or features of the subject invention, there is illustrated in FIG. 1 a valve assembly in accordance with the present invention and designated generally by reference number 100. Valve assembly 100 is adapted for use in a variety of applications, such as for example, medical, consumer beverage, pharmaceutical containers, automobile, household appliance and marine. Valve 100 includes, inter alia, a valve housing 10 having an upper body portion 20 and a lower body portion 30 and a generally spherical valve member 50. The upper and lower body portions 20/30 of the housing 10 define an internal chamber 16 for accommodating the valve member 50 and a central axis "X" for the valve. The housing 10 also has axially aligned inlet and outlet ports, 12 and 14 respectively, formed in the upper and lower body portions, 20 and 30 respectively.

Figure 3B:
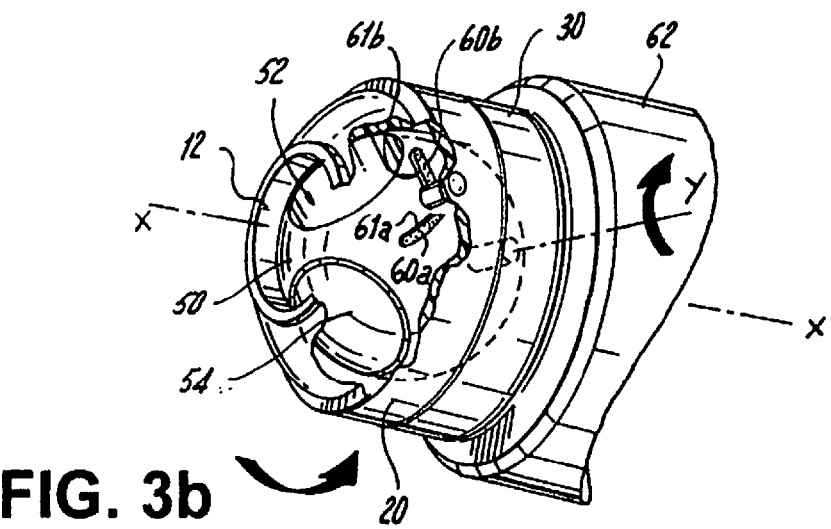
Figure 3C:
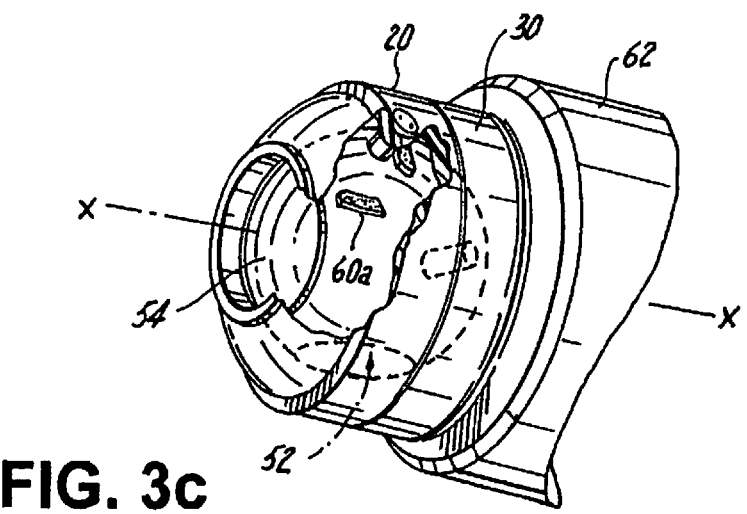

The generally spherical valve member 50 is seated within the internal chamber 16 of the valve housing and has an axial bore 52 extending therethrough. The valve member 50 is mounted for movement within the internal chamber 16 of the housing 10 between an open position and a closed position. FIG. 3a illustrates valve assembly 100 in the open position; wherein the axial bore 52 of the valve member 50 is axially aligned with the inlet port 12 and outlet port 14 of the valve housing 10. In a like manner, FIG. 3c illustrates the valve assembly 100 in the closed position; wherein the axial bore 52 of the valve member 50 is out of alignment with the inlet and outlet ports 12/16 of the valve housing 10. FIG. 3b, provides a detail of the valve assembly 100 in an intermediate position. It should be noted that in FIGS. 3a through 3c, valve assembly 100 is shown mounted on the neck of a container 62.

With continuing reference to FIGS. 3a through 3c, valve member 100 moves between the open position and the closed position when the upper body portion 20 of the housing is rotated about the central axis "X" between about 57 degrees and about 77 degrees with respect to the lower body portion 30. The valve member 100 is mounted for axial rotation within the interior chamber about an axis "Y" (see FIG. 3b) extending perpendicular to the central axis "X" defined by the upper and lower body portions 20/30 of the valve housing 10.

The valve member 50 includes a sealing surface 54 which is adapted for sealing engagement with annular valve seat 18 formed in the housing 10 when the valve is in the closed position. In applications where a pressure is applied to the fluid or air that is metered by the valve assembly, the sealing surface 54 of the valve member 50 includes an annular recess 56 (see FIG. 2) having an o-ring (not shown) disposed therein.

Diametrically opposed pivot pins 58 (only one pin is shown in FIG. 2) extend radially outwardly from the surface of valve member 50 for accommodation within diametrically opposed recesses 32a and 32 formed in the lower body portion 30 of the housing 10 to facilitate the axial rotation of valve member 50.

A camming mechanism is operatively associated with the valve housing 10 and the valve member 50 for moving the valve member 50 between the open position of FIG. 3a and the closed position of FIG. 3c. The camming mechanism includes cam lobes 60a, 60b formed on the exterior surface of the valve member 50 and a cam pin 22 which extends radially inwardly from the interior surface of the upper body portion 20 of the housing 10 to cooperate with the cam lobes. As will be described in detail herein below, the valve assembly can be equipped with a drive ring which is engaged over the upper body portion of the housing. In such an embodiment, the cam pin can be associated with the drive ring such that the drive ring actuates the valve member.

Referring again to FIG. 3b, the cam lobes 60a, 60b are orientated with respect to the axis of rotation "Y" of the valve member 50 at angles to one another. Each cam lobe 60a, 60b has a leading edge 61a, 61b that interacts with the cam pin 22. This interaction facilitates movement of the valve member 50 when the upper body portion 20 is rotated about the longitudinal axis X of the valve assembly 100. When the valve member 50 is moved between the open and closed positions, it is rotated about the pivot axis "Y" which extends through the pivot pin 58 of valve member 50, as illustrated in FIG. 3b.

Those skilled in the art would readily appreciate that in lieu of the cam lobes 60a and 60b, a single arcuate recess or pair of recesses can be formed in the exterior surface of valve member 50. In this embodiment, the length of cam pin 22 would be selected so that it extends into the camming recess(es) and actuates the valve member 50 between the open and closed positions upon the relative axial rotation of the two body portions 20/30 of the housing 10 with respect to each other.

Referring again to FIGS. 2 and 3, the lower body portion 30 of valve assembly 100 has a female thread series 34 formed thereon for engaging with corresponding male series associated with a receptacle (e.g. bottle, container, etc.), tubing or the like. Ribbed surface 36 is provided on the exterior of the lower body portion 30 of the housing 10 to facilitate the rotational engagement of the threads.

A water pressure test was conducted on a valve assembly similar to that described above. The entire valve was manufactured from a rigid thermoplastic and did not include O-ring seals. The camming lobes were constructed such that 67 degrees of rotation was required to move the valve between the open and the closed position. The axial bore of the valve was approximately ¾" in diameter. Six feet of water was applied to the valve through a ⅜" tube that was secured to the valve outlet. No leaking of the valve was observed and therefore, it was concluded that this embodiment of the valve assembly was capable of sealing fluid at a pressure of 3 psi (minimum).

Referring now to FIG. 4, there is illustrated an alternative embodiment of the valve assembly of the present invention designated generally by reference numeral 200. Valve 200 is similar in structure and operation to valve assembly 100. However, unlike valve assembly 100, valve assembly 200 includes a frangible ring 270 which is adapted to be engaged with the housing (i.e., the upper and lower body portions 220, 230) of the valve assembly 200. The frangible ring 270 has been added to valve assembly 200 to provide a visual indication of whether the valve has been previously opened. Frangible ring 270 is molded around the upper and lower body portions 220, 230 of the housing so that when the body portions are rotated relative to each of the, the ring 270 is broken. Such a tamper-proof feature would be useful in applications where the valve is with consumer beverages, for example.

Referring now to FIG. 5 which illustrates a further embodiment of the valve assembly of the present invention that has been designated by reference number 300. Valve 300 is similar in structure and operation to valve assembly 100. However, unlike valve 100, valve 300 includes a frangible sealing disc 370 which is positioned within the interior chamber 316 defined, in part, by the lower body portion of the housing. Frangible sealing disc 370 can function as a tamper-proof feature, as well as, provide an additional seal for valve assembly 300. In this embodiment, the valve member 350 has a shape protuberance 364 formed on its exterior surface. When the valve member 350 is rotated from the open to the closed position the protuberance 364 punctures the sealing disc 370 allowing fluid or air to flow through the valve member 350 when it is returned to the closed position.

Figure 6:
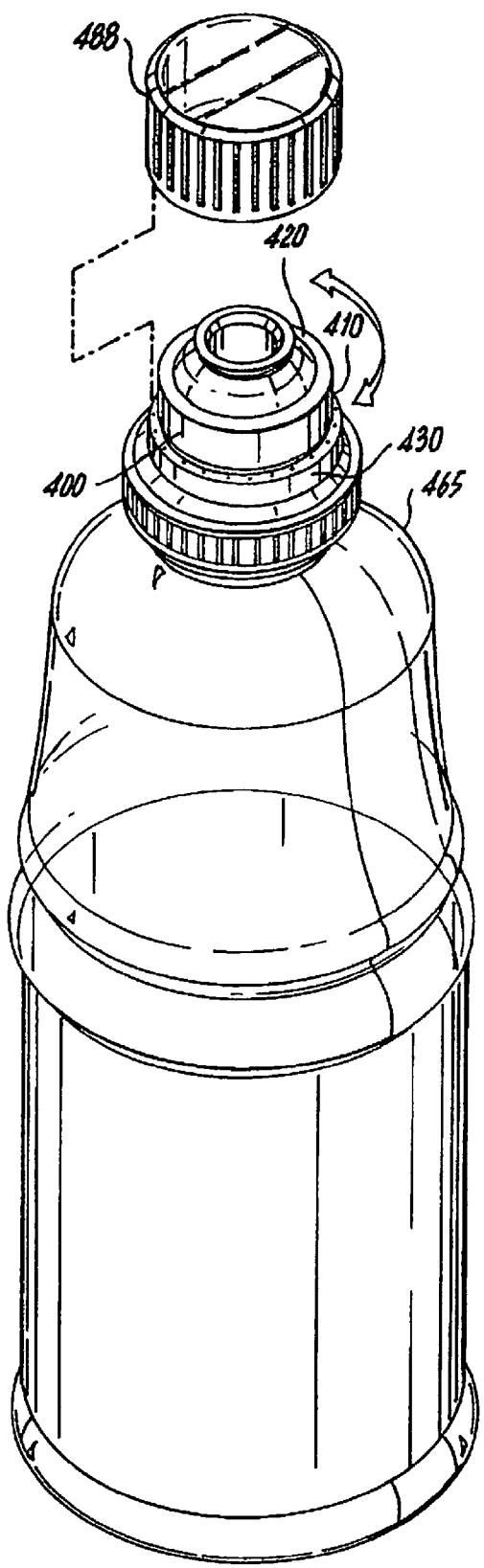
FIG. 6 is a perspective view of a valve assembly constructed in accordance with an alternative embodiment of the subject invention, wherein the valve assembly is engaged with a beverage container and is adapted for engagement with a cap.
Figure 7:
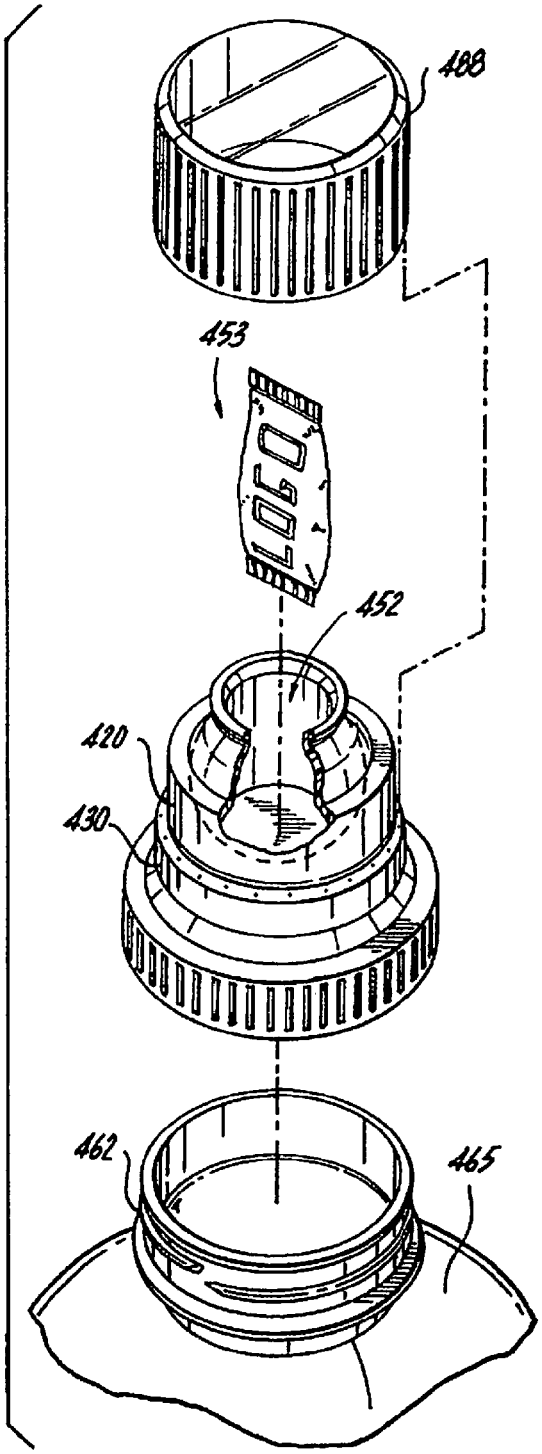
FIG. 7 is a perspective view of a valve assembly constructed in accordance with an alternative embodiment of the subject invention with parts separated for ease of illustration, wherein a prize is stored within the bore formed in the valve member.

Referring now to FIGS. 6 and 7, which illustrate yet another embodiment of the valve assembly of the present invention designated generally by reference numeral 400. Valve assembly 400 is similar in structure and operation to valve assembly 100. As shown in these figures, valve assembly 400 is threadably engaged with the neck 462 of container 465. A cap 488 is provided which engages with the upper portion 420 of the valve assembly 400. Like the previously disclosed valve assemblies, valve member 450 has an axial bore 452 formed therein which allows fluid or air to flow through the valve assembly 400 when the valve member 450 is in the open position. Still further, the axial bore 452 is adapted for receiving and storing an article of manufacture 453 or fluid, such as for example, a prize, a ticket, a vitamin supplement, or a medication. In such embodiments, it would be advantageous to insert a sealing disc into the valve assembly similar that disclosed with reference to FIG. 5 to prevent to article of manufacture from falling into the container during storage. Alternatively, a removable seal can be placed over the mouth of container 462.

Figure 8:
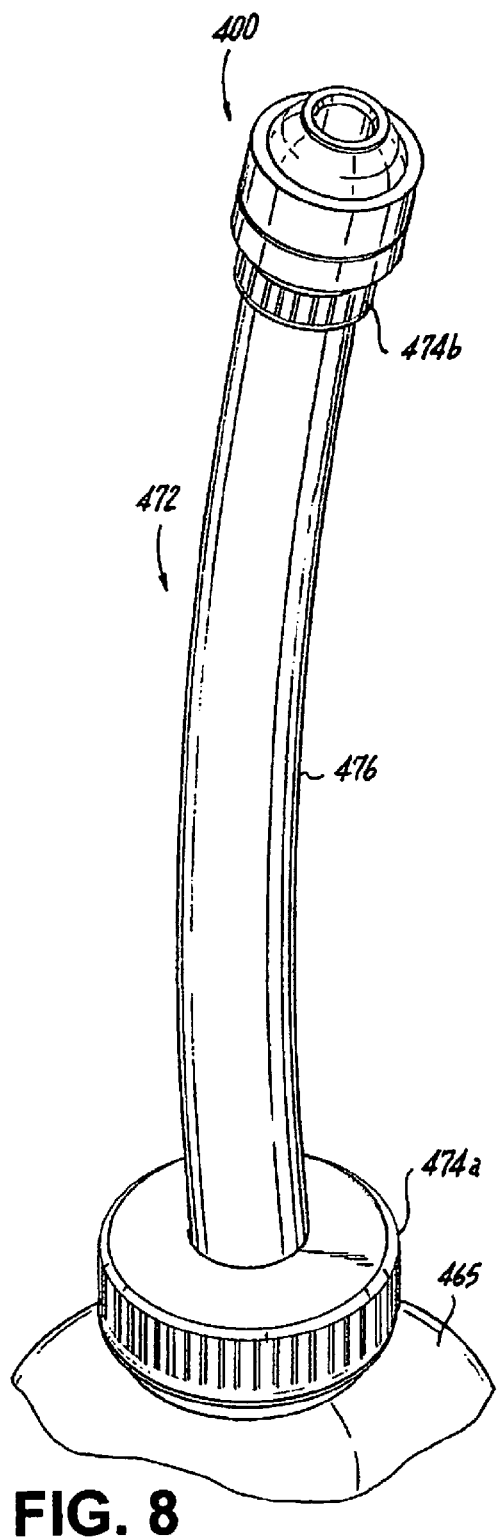
FIG. 8 is a perspective view of a valve assembly constructed in accordance with a further alternative embodiment of the subject invention, wherein the valve assembly is mounted on the end of a tubing which is in fluid communication with a container.
Figure 9:
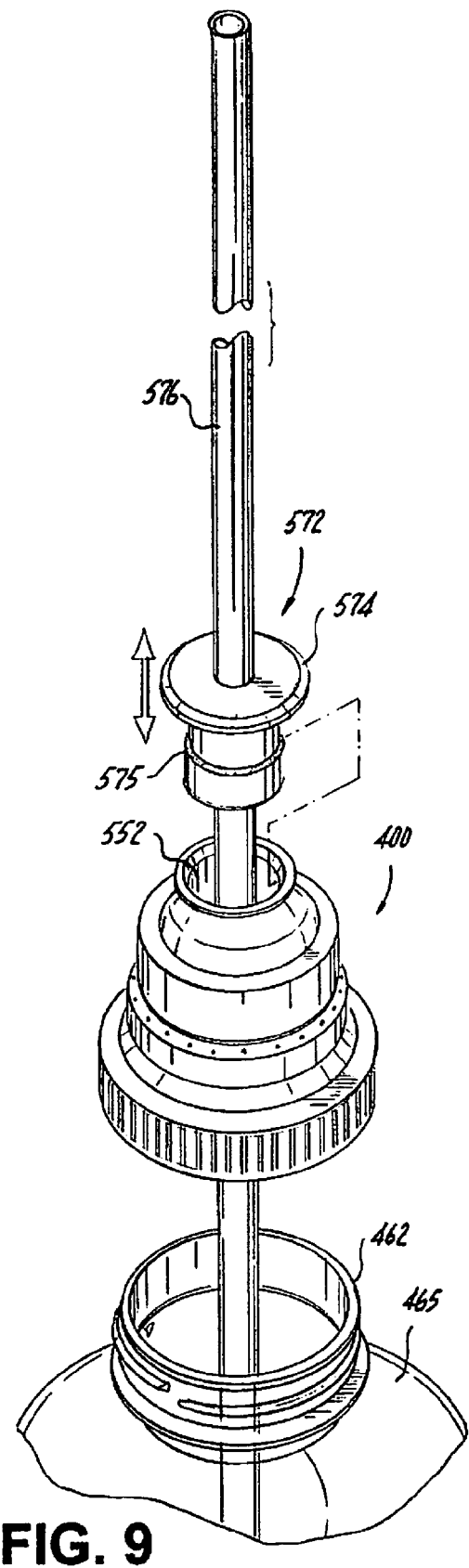
FIG. 9 is a perspective view of a valve assembly constructed in accordance with a further alternative embodiment of the subject invention, wherein the valve assembly is mounted on a container and a straw assembly is position within the open valve.

Referring now to FIGS. 8 and 9 which illustrate an alternate application for valve 400. In FIG. 8, valve 400 is mounted on the end of a tubing assembly 472. Tubing assembly 472 includes two end connectors 474a, 474b and an elongated tube 476. End connector 474a is threadably engaged with the neck of container 465 and includes a central aperture which is adapted to allow tube 476 to telescope in and out of container 465. Valve assembly 400 is engaged with end connector 474b such that when the valve is in the open position, fluid can flow from the container 465 through the tubing assembly 472 and out of the valve 400.

FIG. 9 illustrates valve assembly 400 mounted on the neck 462 of container 465. Valve assembly 400 is shown in the open position having straw assembly 572 inserted into the axial bore 552. Straw assembly 572 includes a straw 576 and a plug member 574. The plug member 574 has a circumferential O-ring 575 and is adapted for sealing engagement with the inlet port of valve 400.

Figure 10:
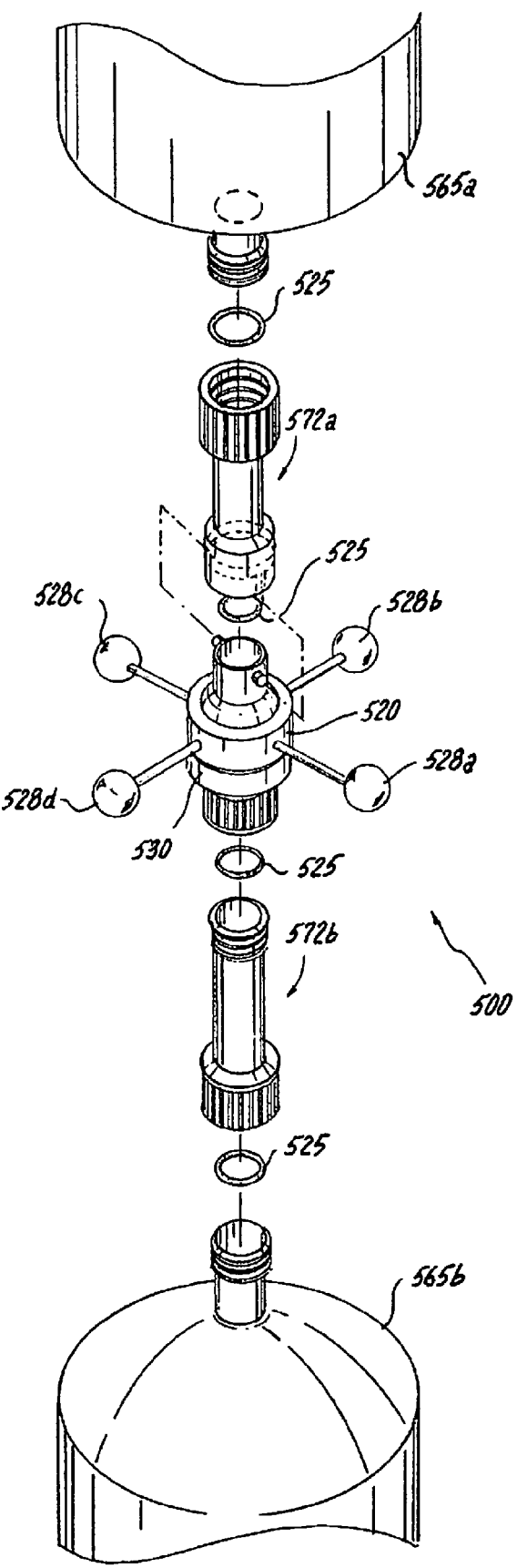
FIG. 10 is a perspective view of the valve assembly of the present disclosure which illustrates the valve positioned between two containers.

Referring now to FIG. 10, which illustrates a further embodiment of the valve assembly of the present invention, designated generally by reference numeral 500. As shown herein, valve assembly 500 is being used to meter the flow between two containers 565a, 565b. The flow path between the containers includes upper and lower conduit assemblies 572a, 572b and valve assembly 500. The conduit assemblies are sealingly engaged between containers 565a, 565b and the valve assembly 500.

Valve assembly 500 is similar in structure and function to valve assembly 100. However, unlike valve assembly 100, valve assembly 500 includes actuator arms 528a through 528d that facilitate the relative rotation of the upper body portion 520 of the valve assembly 500 with respect to the lower body portion 530 thereby moving the valve member between the open and closed positions. O-rings 525 are provided to seal the connections of the components and prevent leakage from the flow path.

Figure 11:
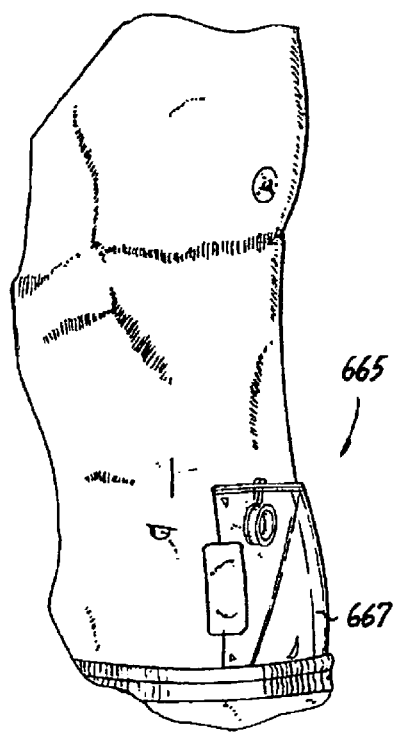
FIG. 11 is a perspective view of the valve assembly of the present disclosure adapted for use with a colostomy bag.
Figure 12:
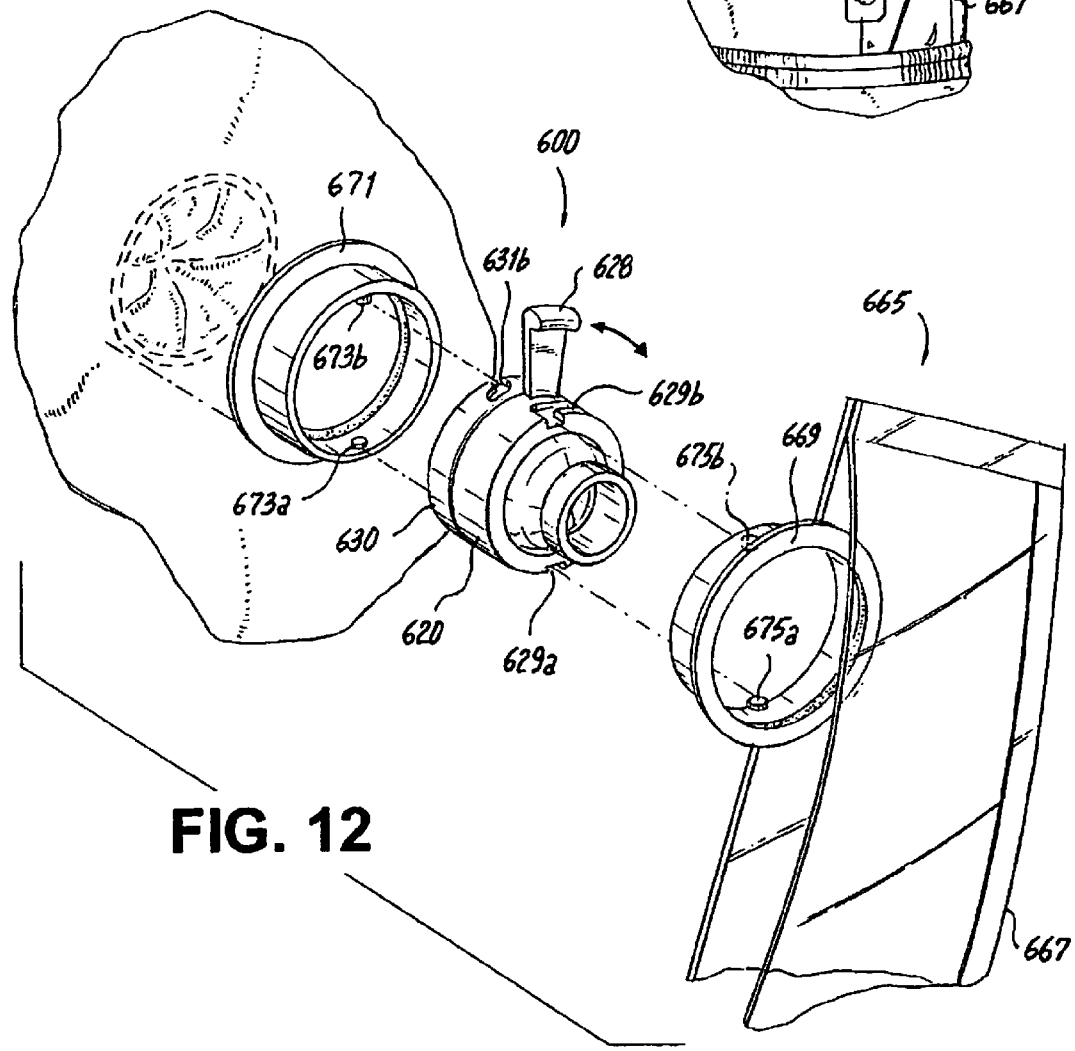
FIG. 12 is a perspective view of the valve assembly of FIG. 11 with parts separated for ease of illustration.

Referring now to FIGS. 11 and 12, wherein valve assembly 600 is shown used in conjunction with a colostomy bag assembly 665. Colostomy bag assembly 665 includes a bag 667, a proximal ring 669 and a distal ring 671. The proximal ring 669 has an outer flange that is sealingly engaged with the bag 667. Two retaining pins 675a, 675b are formed on the inside diameter of the proximal ring 669. These pins 675a, 675b are inserted into corresponding engagement recesses 629a, 629b formed in valve assembly 600 and secure the valve assembly 600 to the proximal ring 669. Similarly, distal ring 671, which is secured to the surface of the patient's body, includes retaining pins 673a, 673b that are inserted into corresponding engagement recesses 631a (not show), 631b formed in valve assembly 600. Valve assembly 600 has been equipped with an actuator arm 628 which allows the patient to move the valve between the open and the closed position as desired.

Figure 13:
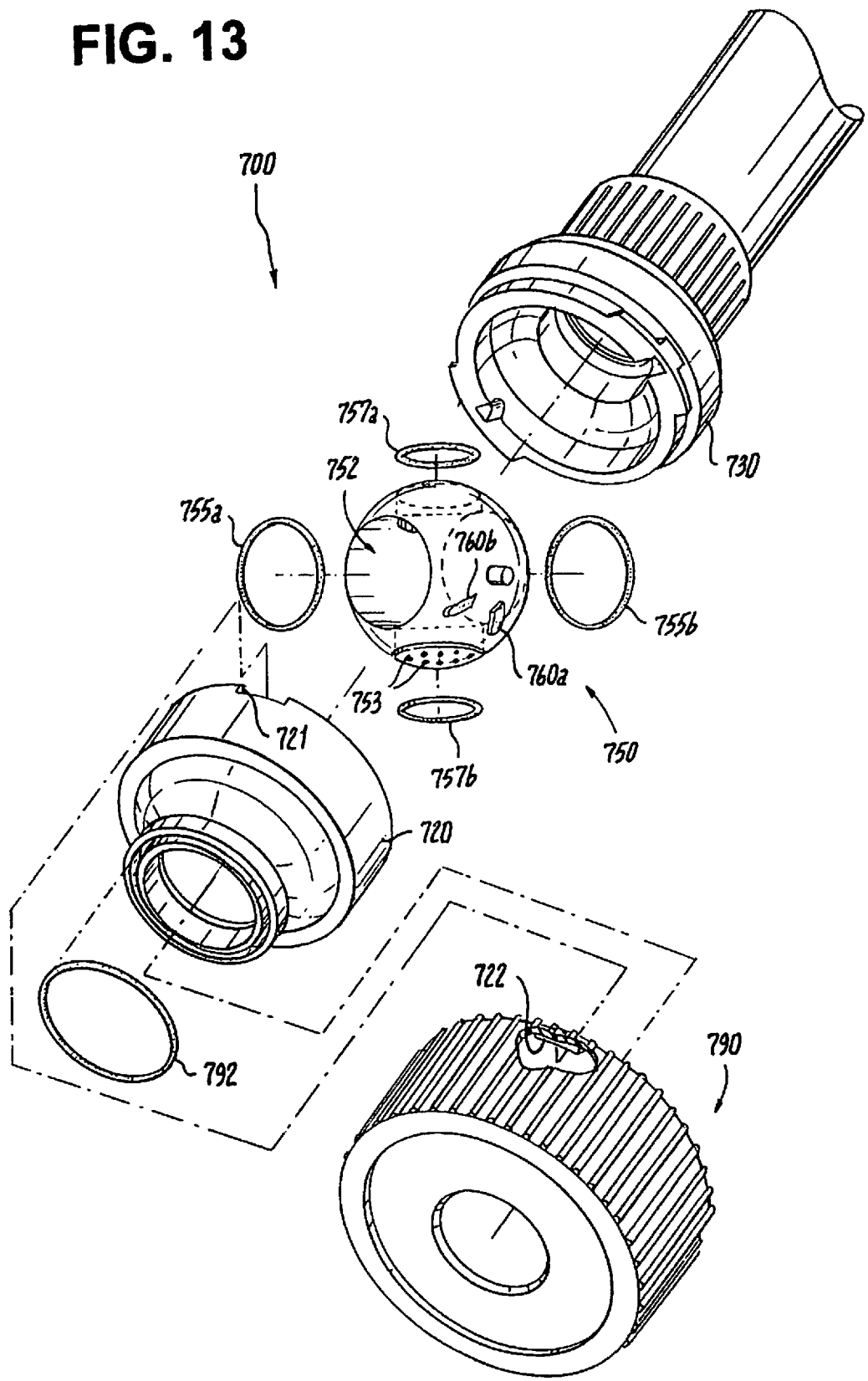
FIG. 13 is an exploded perspective view of an alternative embodiment of the presently disclosed valve assembly with parts separated for ease of illustration, wherein the valve member includes a plurality of flow passages extending through the valve perpendicular to the central bore.

Referring now to FIG. 13, there is illustrated showerhead which includes a valve assembly constructed in accordance with an alternative embodiment of the present invention and designated by reference numeral 700. Again, valve assembly 700 is similar in structure and operation to the previously disclosed valves, but unlike the prior valves, valve assembly 700 has a plurality of flow passages 753 formed in the valve member 750.

The flow passages 753 extend along an axis that is perpendicular to the axial bore 752 such that when the valve member is in the closed position, fluid traverses the valve through the plurality of flow passages 753. Hence when the valve assembly 700 is in the open position, a single jet of water is emitted from the showerhead assembly and when it is in the closed position, water streams from the flow passages 753. O-ring seals 755a, 755b and 757a, 757b are provided at both ends of the axial bore 752 and flow passages 753 to properly seal the valve when in the open and closed positions, respectively.

The showerhead disclosed in FIG. 13 is also equipped with a control ring 790 that sealingly engages with the upper portion 720 of the valve assembly 700 using O-ring seal 792. Control ring 790 has a drive pin 722 formed on its interior surface. Drive pin 722 projects through the slot 721 formed in the upper portion 720 of the valve assembly 700 and engages with the cam lobes 760a, 760b formed the valve member 750. Thus, rotation of the control ring 790 with respect to the lower body portion 730 of the valve assembly 700 moves the valve member between the open and the closed positions.

Those skilled in the art will readily appreciate that the showerhead assembly described hereinabove can be adapted for use for metering an air supply rather than fluid.

Figure 14:
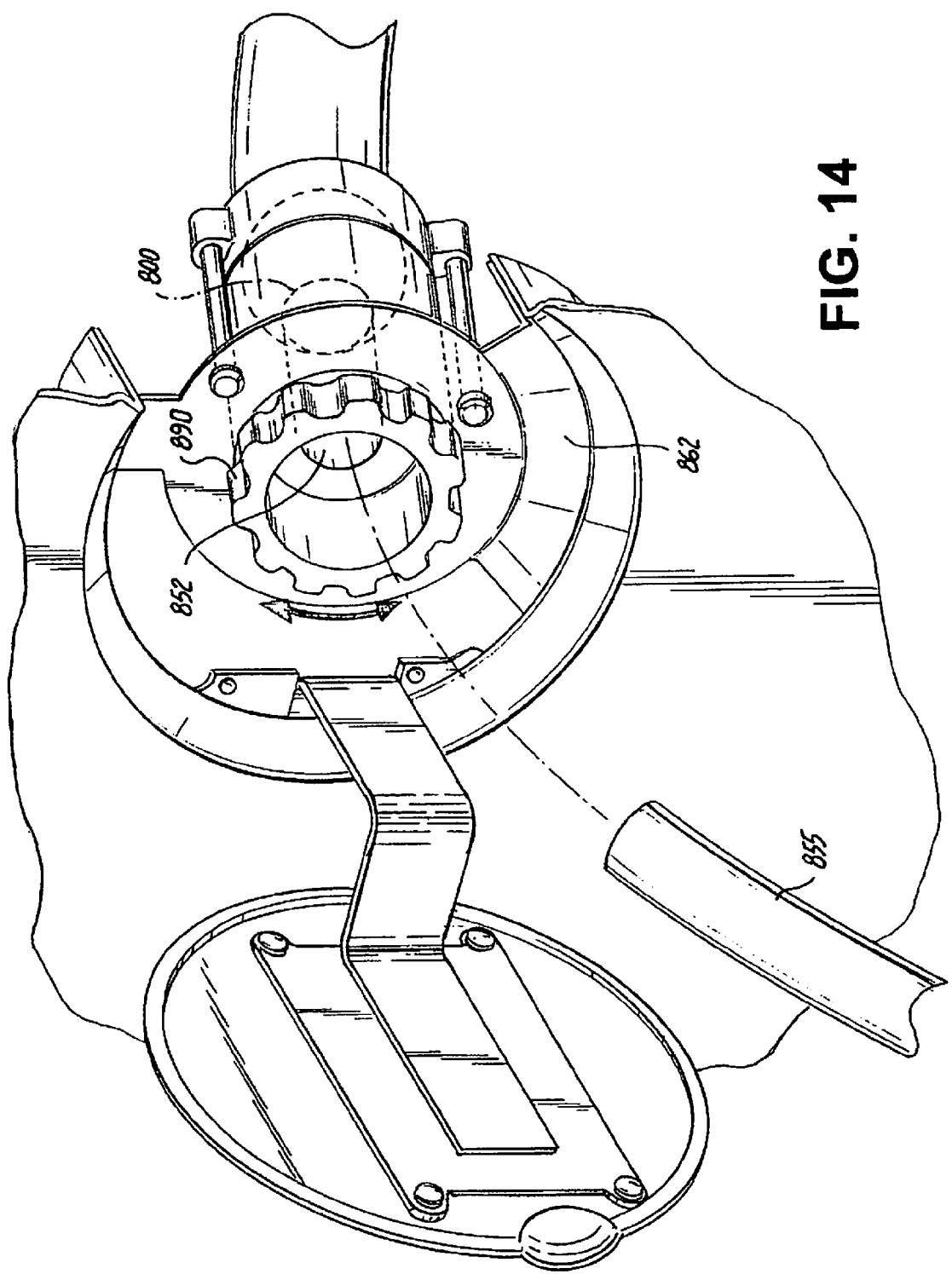
FIG. 14 is a perspective view of an alternative application for the valve assembly of the present invention, wherein the valve is used in a automobile fuel tank.

Referring now to FIG. 14 which illustrates a valve assembly (designated by reference numeral 800) constructed in accordance with the present invention positioned within the inlet 862 of fuel tank. The use of valve assembly 800 in this application allows for the elimination of a removable gas cap and only requires an approximately 67 degrees rotation of drive ring 890 to open the valve. The axial bore 852 of the valve member would be adapted for receiving a standard fuel pump nozzle 855.

Referring now to FIGS. 15 and 16, there is illustrated a surgical instrument constructed in accordance with a preferred embodiment of the subject invention and designated generally by reference numeral 900.

Minimally invasive surgical procedures are commonly performed by passing surgical instruments through a narrow tube or cannula inserted through a small entrance incision formed in a patient's body using a trocar or obturator. For example, laparoscopic surgical procedures are performed within the abdominal cavity through small incisions formed in the abdominal wall. During a laparoscopic procedure, insufflating gases are introduced into the abdominal cavity to raise the abdominal wall or peritoneum away from the vital organs within the abdominal cavity, thereby providing an adequate region in which to operate.

During a laparoscopic procedure, it is necessary to maintain the atmospheric integrity of the abdominal cavity, and thus prohibit the egress of insufflation gases for the surgical site. It is common therefore, to provide a seal assembly within the cannula so that when instruments are present within the cannula and when instruments are withdrawn form the cannula, the tubular passageway extending therethrough is tightly sealed to prevent the egress of insufflating gases. For example, it is known to employ an elastomeric seal member with an aperture or slit that may be forced open when the instrument is passed therethrough. The seal member prevents the egress of insufflation gasses when the instrument is present and absent from the cannula. There are known disadvantages to employing such seals. In particular, the opening or slit can tear when an instrument is forced therethrough, thus rendering the seal in effective to prevent the egress of insufflating gases from the cannula sleeve.

Therefore as will be described hereinbelow, surgical instrument 900 has been equipped with the valve assembly of the present invention to prevent the egress of insufflating gases through the cannula in the absence of a surgical instrument. Surgical instrument 900 is intended for use as an access device, and more particularly, as a device to facilitate the introduction of a surgical instrument into a person's body during a minimally invasive surgical procedure. Surgical instruments introduced into a patient's body through the surgical instrument 900 of the subject invention can include, for example, clip appliers, graspers, dissectors, retractors, staplers, laser fibers, photographic devices, endoscopes, laparoscopes, tubes; and the like.

Surgical instrument or access device 900 includes a proximal valve housing 910 having an inlet port 912 for receiving surgical instruments. Valve housing 910 includes an upper body portion 920 and a lower body portion 930 which define, among other things, a generally hemispherical internal chamber 916 for accommodating a generally spherical valve member 950. Internal chamber 916 communicates with an outlet port 914 of the valve housing 910 which is axially aligned with the inlet port 912. Valve housing 910 is operatively associated with a lower cannula housing 980. Preferably, the valve housing 910 and cannula housing 980 are formed of a polycarbonate material.

An elongated cannula sleeve 982 extends distally from the cannula housing 980. Cannula sleeve 982 has an elongated passageway 984 extending therethrough, which defines a longitudinal axis defined by reference character "X". Passageway 984 is axially aligned with the inlet port 912 and outlet port 914 of valve housing 910. Cannula sleeve 982 may be formed of stainless steel or another suitable rigid material such as polycarbonate materials or the like. An inlet conduit 986 is incorporated into cannula housing 980 to permit the passage of insufflation gases through the cannula sleeve 982 and into the patient's body cavity. The inlet conduit 986 can include a stopcock valve, which is not shown.

Valve member 950, which is preferably formed from a polycarbonate material, is mounted for axial rotation within the interior chamber 916 about an axis extending perpendicular to the longitudinal axis of the cannula sleeve 982. Diametrically opposed pivot pins 958 (only one pin is shown in FIG. 16) extend radially outwardly from the surface of valve member 950 for accommodation within diametrically opposed recesses 932a, 932b to facilitate the axial rotation of valve member 950. An axial bore 952 extends through the valve member 950, and a convex sealing surface 954 is provided on valve member 950, spaced from axial bore 952.

Figure 17A:
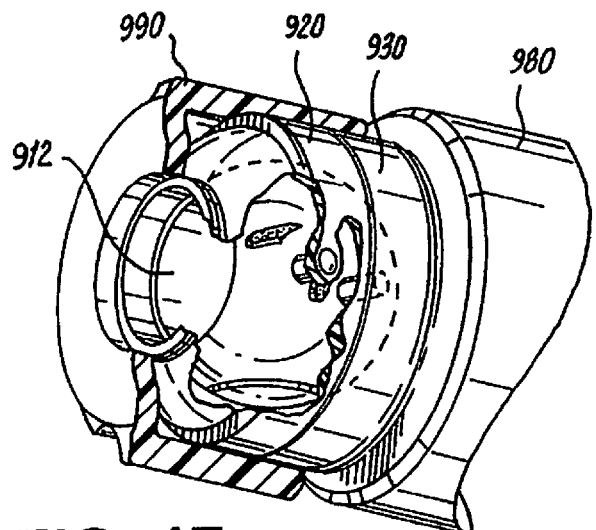
FIG. 17a is a perspective view in partial cross-section of the valve housing, which forms part of the surgical access device of FIG. 15, wherein the valve member is shown in an open position with the axial bore of the valve member aligned with the axially aligned inlet and outlet ports of the valve.
Figure 17B:
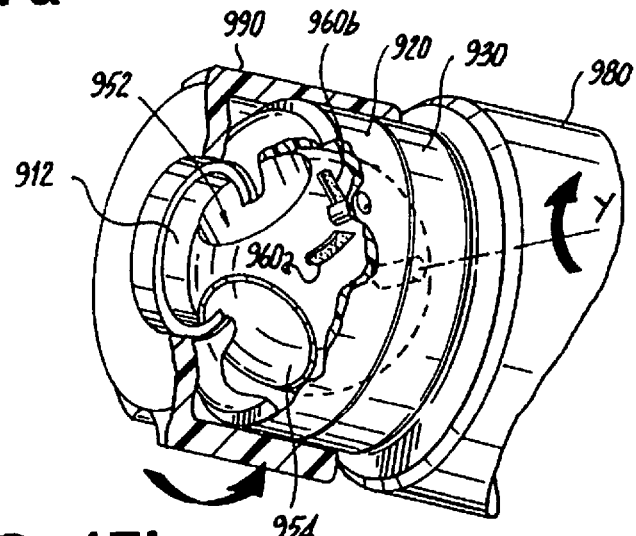
FIG. 17b is a perspective view in partial cross-section of the valve housing of the subject invention, wherein the valve member is in transition from the open position of FIG. 17a to the closed position of FIG. 17c.

Valve member 950 is mounted for movement between an open position and a closed position. In the open position of valve member 950, which is shown in FIG. 17a, the axial bore 952 is axially aligned with the elongated passageway 984 of cannula sleeve 982 and the inlet and outlet ports 912, 914 of valve housing 910. In the closed position of valve member 950, which is shown in FIG. 17c, the axial bore 952 extends perpendicular to the elongated passageway 984 of cannula sleeve 982 and the sealing surface 954 is axially aligned with the inlet port 912 of valve housing 910.

Figure 17C:
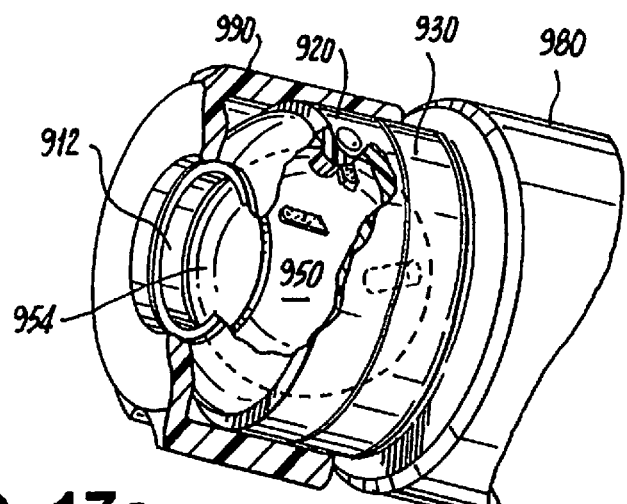
FIG. 17c is a perspective view in partial cross-section of the valve housing of the subject invention, wherein the valve member is disposed in a closed position so that the axial bore of the valve member is oriented perpendicular to the axially aligned inlet and outlet ports of the valve housing.

As described with respect to previous embodiments, a camming mechanism is operatively associated with the valve housing 910 and the valve member 950 for moving the valve member 950 between the open position of FIG. 17a and the closed position of FIG. 17c. The camming mechanism includes arcuate cam lobes 960a, 960b formed on the exterior surface of the valve member 950 and a cam pin 922 which extends radially inwardly from the interior surface of the upper housing portion/drive ring 920 to cooperate with the cam lobes. As before, a leading edge of the cam lobes 960a, 960b interacts with the cam pin 922. This interaction facilitates movement of the valve member 950 when the drive ring 920 is rotated about the longitudinal axis "X" of cannula sleeve 982. When the valve member 950 is moved between the open and closed positions, it is rotated about the pivot axis "Y" which extends through the pivot pin 958 of valve member 950, as illustrated in FIG. 3b.

Drive ring 920 is rotatably mounted on the proximal end of valve housing 910 and includes diametrically opposed radially inwardly extending guide ribs 924 which cooperate with an annular guide surface 938 formed on the exterior of the lower body portion 930 of the valve housing 910. Stop surfaces 940 limit the rotational motion of upper body portion/drive ring 920 relative to the longitudinal axis of the cannula sleeve 982.

A fluted manipulation knob 990 is cooperatively engaged with the drive ring 920. Manipulation knob 990 includes inlet port 992, which is aligned with the axial passageway 984 of cannula sleeve 982 and defines in part the inlet port 912 of valve housing 910. The engagement of drive ring 920 and manipulation knob 990 is accomplished through the coupling of a pair of diametrically opposed radially outwardly extending engagement tabs 926 on drive ring 920 (only one tab is shown in FIG. 16) with a pair of corresponding diametrically opposed interior recess 994a, 994b formed in the interior cavity of manipulation knob 990. Alternative structural means may be provided to enable ready manipulation of drive ring 920.

A flange 942 projects radially outwardly from the lower portion 930 of valve housing 910 to provide leverage to the surgeon when the manipulation knob 990 is rotated. Valve housing 910 further includes a membrane seal 996 located proximal to the interior chamber 916 and retained within an annular recess. Membrane seal 996 has a central slitted opening 998 that is axially aligned with the outlet port 912 of valve housing 910 and the passageway 984 of the cannula sleeve 982. Central opening 998 is dimensioned and configured to accommodate the passage of a surgical instrument therethrough. The membrane seal 996 will help to prevent the egress of insufflation gasses from the access device 900 when an instrument is present therein and the valve member 950 is in an open position.

Referring now to FIGS. 18 and 19, there is a perspective view of another embodiment of the surgical access device of the subject invention, which is designated by reference numeral 1000 and includes a detachable valve housing 1010. More particularly, as best seen in FIG. 5, the valve housing 1010 is detachably connected to the cannula housing 1080. This will enable a surgeon to utilize the cannula housing 1080 during the performance of procedures in which the valve housing is not required. It will also enable the surgeon to readily remove specimens from the surgical site. As illustrated, the detachable relationship of valve housing 1010 and cannula housing 1080 is facilitated by a threaded connection therebetween. Alternative coupling arrangements are envisioned and well within the scope of the subject disclosure.

Although the valve assembly of the subject invention and surgical access device incorporating the same have been described with respect to preferred embodiments, those skilled in the art will readily appreciate that changes and modifications may be made thereto without departing from the spirit and scope of the subject invention as defined by the appended claims.

Additionally, the valve assembly of the subject invention can be used in alternative applications not described hereinabove. For example, the valve can be installed in a sink drain to eliminate the need for a plug. Additionally, the valve can replace bungs or plugs used to seal penetrations in the hull of boats. Still further, the valve can replace caps on hand creams, toothpaste, etc.

As set forth above, the surgical access device of the present disclosure may, according to various embodiments, provide for a valve member having more than one lumen/bores extending therethrough, e.g., FIG. 13 (as used herein, the terms "lumen" and "bore" are intended to be synonymous). A further example of such an arrangement is set forth below. While the example embodiment discussed hereinbelow relates to a valve member for a surgical device that provides a substantial seal between a body cavity of a patient and the outside atmosphere before, during and after insertion and manipulation of an instrument through the seal, the embodiment shown and its description in the surgical context is merely illustrative. It should be recognized that the principles described hereinbelow and illustrated in FIGS. 20-22c are equally applicable in any of the other types of valves described in this application, e.g., consumer beverage, pharmaceutical containers, automobile, etc.

More specifically, the below-referenced embodiment of a surgical access device of the present disclosure contemplates the introduction and manipulation of various types of instrumentation adapted for insertion through a trocar and/or cannula assembly while maintaining a substantially fluid-tight interface about the instrument to preserve the atmospheric integrity of a surgical procedure from leakage. Examples of instrumentation include, but are not limited to, clip appliers, graspers, dissectors, retractors, staplers, laser probes, photographic devices, endoscopes and laparoscopes, tubes, and the like. Furthermore, these instruments can be designed with a variety of tip configurations and a variety of diameters. Such instruments will collectively be referred to as "instruments" or "instrumentation" or "surgical objects."

Particular embodiments of the present disclosure will be described herein with reference to the accompanying drawings. As shown in the drawings and as described throughout the following description, and as is traditional when referring to relative positioning on an object, the term "proximal" refers to the end of the device that is closer to the user and the term "distal" refers to the end of the device that is farther from the user. In the following description, well-known functions or constructions are not described in detail to avoid obscuring the present disclosure in unnecessary detail.

Referring now to the drawings, in which like reference numerals identify identical or substantially similar parts throughout the several views, FIG. 20 illustrates a surgical access device designated generally by reference numeral 2100. In accordance with the present disclosure, the surgical access device 2100 includes a portal 2110 having a proximal end 2110a and a distal end 2110b, the distal end 2110a being dimensioned for insertion within tissue to access an underlying tissue site. The portal 2110 defines a longitudinal axis "X" and has a longitudinal opening 2112 disposed at the proximal end 2110a for reception of a surgical object "I."

Referring now to FIGS. 20 and 21, the portal 2110 includes a cannula housing 2114 disposed at the proximal end 2110a and an elongated cannula 2116 disposed at the distal end 2110b and extending distally from the cannula housing 2114. The cannula housing 2114 includes an upper body portion 2114a and a lower body portion 2114b which define, among other things, a generally hemispherical internal chamber 2115 (FIGS. 22a-22c) for accommodating a generally spherical valve 2120 in mechanical cooperation. The internal chamber 2115 communicates with an outlet 2117 of the cannula housing 2114 which is axially aligned with the longitudinal opening 2112 and the cannula 2116. The cannula housing 2114 may be formed of a polycarbonate material.

Referring again to FIGS. 20 and 21, the cannula 2116 has an elongated passageway 2118 extending therethrough. The passageway 2118 is axially aligned with the longitudinal opening 2112 and outlet 2117 of the cannula housing 2114. The cannula 2116 may be formed of stainless steel or another suitable rigid material such as polycarbonate materials or the like. An inlet conduit 2119 may be incorporated into the cannula housing 2114 to permit the passage of insufflation gases through the cannula 2116 and into the patient's body cavity.

Figure 22A:
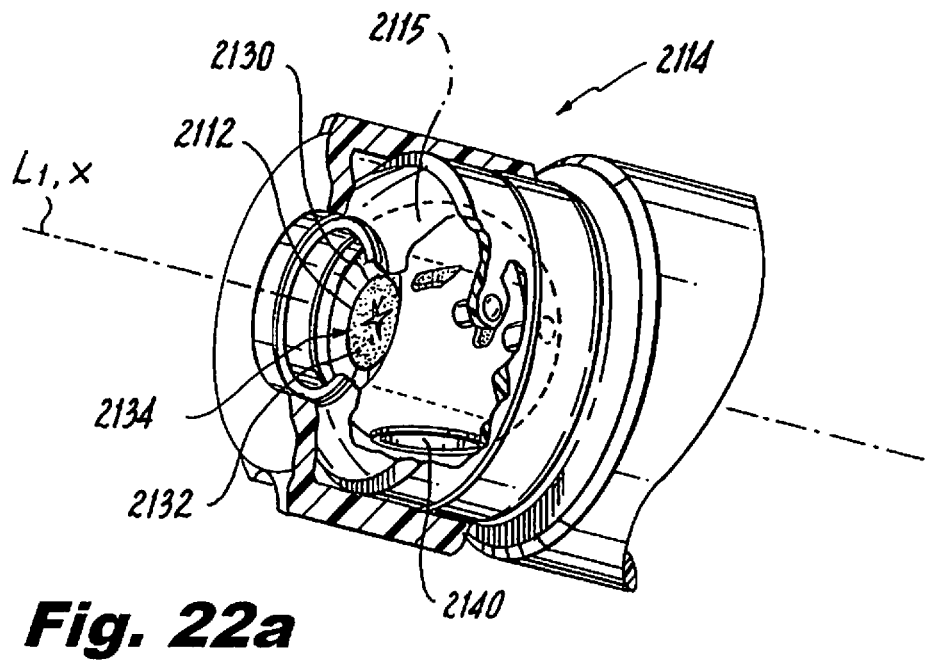
FIG. 22A is a perspective view in partial cross-section of the cannula housing, which forms part of the surgical access device of FIGS. 20-21, wherein a valve seated in the cannula housing is shown in a first orientation with a longitudinal axis of a first lumen of the valve aligned with a longitudinal axis of a portal of the surgical access device.
Figure 22B:
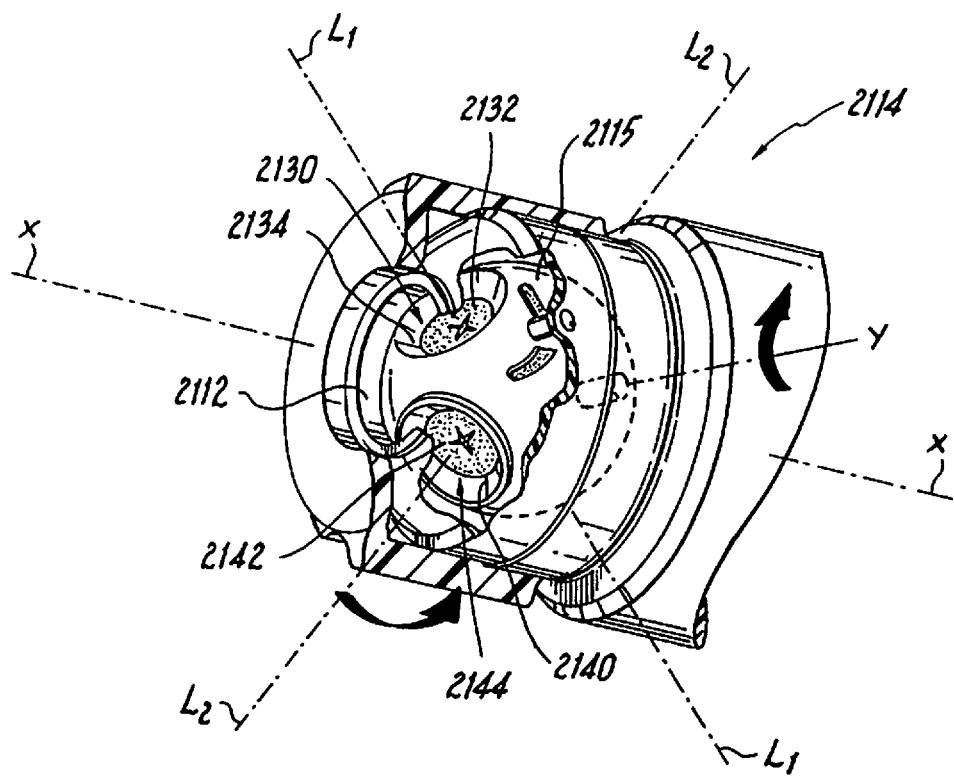
FIG. 22B is a perspective view in partial cross-section of the cannula housing of the present disclosure, wherein the valve is disposed in transition from the first orientation of FIG. 22A to a second orientation of FIG. 22C.
Figure 22C:
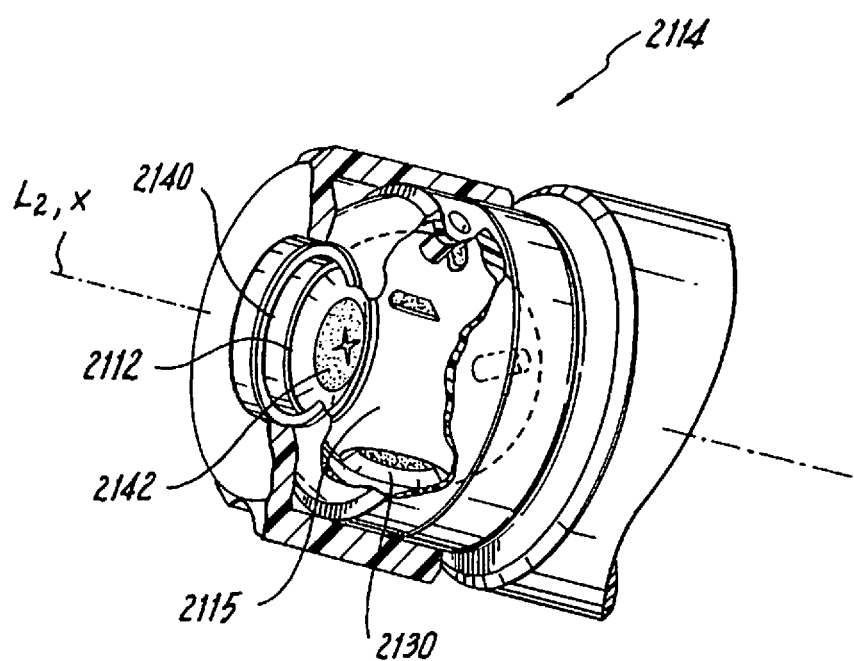
FIG. 22C is a perspective view in partial cross-section of the cannula housing of the present disclosure, wherein the valve is shown in a second orientation with a longitudinal axis of a second lumen of the valve aligned with the longitudinal axis of the portal of the surgical access device of FIGS. 20-22B.

Referring now to FIGS. 20-22c, the valve 2120, which is preferably formed from a polycarbonate material, defines first and second lumens 2130, 2140 therethrough and is mounted for axial rotation within the internal chamber 2115 about a transverse axis "Y" (FIG. 22B). Transverse axis "Y" extends perpendicular to the longitudinal axis "X" of the portal 2110. Each lumen 2130, 2140 includes one or more seals 2132, 2142 disposed therein. Each seal 2132, 2142 defines a passage 2134, 2144 for reception of the surgical object "I" in substantial sealed relation therewith. The valve 2120 is selectively positionable between a first orientation (FIG. 22a) and a second orientation (FIG. 22c), passing through one or more transition orientations (FIG. 22b). Each lumen 2130, 2140 may be disposed in substantial alignment with the longitudinal opening 2112 and/or the longitudinal axis "X" of the portal 2110. More particularly, each lumen 2130, 2140 defines a respective longitudinal axis "L1", "L2" wherein each longitudinal axis "L1", "L2" of each lumen 2130, 2140 may be separately configured to be selectively positioned in substantial alignment with the longitudinal axis "X" of the portal 2110 whereby the longitudinal axis "L1", "L2" of the respective lumen 2130, 2140 and the longitudinal axis "X" of the portal 2110 define the passage for reception of the surgical object "I." The longitudinal axis "L1" of the first lumen 2130 may be disposed in substantial alignment with the longitudinal axis "X" of the portal 2110 in the first orientation (FIG. 22*a*) and the longitudinal axis "L2" of the second lumen 2140 may be disposed in substantial alignment with the longitudinal axis "X" of portal 2110 in the second orientation (FIG. 22*c*). As illustrated in FIGS. 21-22*c*, the first lumen 2130 may be disposed substantially orthogonal to the second lumen 2140, although any suitable offset angle between these lumens may be employed. As noted above, in addition to the valve 2120 being selectively positionable between a first orientation (FIG. 22*a*) and a second orientation (FIG. 22*c*), the valve 2120 may also be positionable in a third orientation, such as a transition orientation that is located between the first and second orientations, as shown in FIG. 22*b*, or in a different orientation that is located beyond the first and second orientations. Advantageously, the third orientation may be a "closed" position, such that the inlet and outlet ports of the housing are sealed. Alternatively, the third orientation may be a position in which the inlet and outlet ports of the housing are aligned with a third lumen (not shown) of the valve member. Of course, it should be understood that any number of lumens through the valve member are possible, the lumens having a variety of diameters, e.g., different or possibly the same, may have seals or no seals.

With continued reference to FIGS. 20-22*c*, the first lumen 2130 includes a first seal 2132 and the second lumen 2140 includes a second seal 2142. The first seal 2132 has a first diameter and the second seal 2142 has a second diameter that may be different from the first diameter of the first seal 2132 for receiving different sized instruments in substantial sealing relationship. Each seal 2132, 2142 may also have the same diameter. The seal diameters typically range in size from about 1 mm to about 15 mm. In particular embodiments, one of the two seals may have diameters of 2 mm, 3 mm, or 5 mm and the other seal may have diameters of 10 mm, 12 mm, or 15 mm.

Referring again to FIG. 21, the valve 2120 includes diametrically opposed pivot pins 2122, 2124 (2124 not shown) that extend radially outwardly from the surface of valve 2120 for accommodation within diametrically opposed recesses 2126, 2128 within the cannula housing 2114 to facilitate the rotation of valve 2120 about longitudinal axis "Y."

With continued reference to FIG. 21, the valve 2120 includes a camming assembly 2150 for selectively positioning the valve 2120 between the first and second orientation about a transverse axis "Y" (FIG. 22*b*). The camming assembly 2150 includes a cam surface 2152 formed on an exterior surface of the valve 2120 and a cam pin 2155 formed on a drive ring 2160 located within an interior surface of the upper body portion 2114*a* of the portal 2110 for engaging the cam surface 2152. The cam surface 2152 is defined by a pair of cam lobes 2154, 2156 disposed at an angle relative to each other. The cam pin 2155 extends radially inwardly from the drive ring 2160 mounted on the portal 2110 to cooperate with the cam lobes 2154, 2156. The drive ring 2160 is rotatable about the longitudinal axis "X" of the portal 2110, wherein rotation of the drive ring 2160 causes the valve 2120 to rotate between the first and second orientations about the transverse axis "Y." A fluted manipulation knob 2170 is operatively coupled to the drive ring 2160 for selectively positioning the valve 2120 between the first and second orientations.

In operation, leading edges 2154E, 2156E of the cam lobes 2154, 2156 interact with the cam pin 2155. This interaction facilitates movement of the valve 2120 when the drive ring 2160 is rotated about the longitudinal axis "X." When the valve 2120 is moved between the first and second orientations, the valve 2120 pivots about the transverse axis "Y", which extends through pivot pins 2122, 2124 of valve member 2120, as illustrated in FIG. 22*b*.

Referring again to FIG. 21, the drive ring 2160 is rotatably mounted on the upper body portion 2114*a* of cannula housing 2114 and includes diametrically opposed radially inwardly extending guide ribs 2162*a*, 2162*b* which cooperate with an annular guide surface 2164 formed on the exterior of the lower body portion 2114*b* of the cannula housing 2114. Stop surfaces 2166*a*, 2166*b* (2166*b* not shown) limit the rotational motion of upper body portion 2114*a* and drive ring 2160 relative to the longitudinal axis "X."

With continued reference to FIG. 21, the manipulation knob 2170 is cooperatively engaged with the drive ring 2160. The manipulation knob 2170 is disposed in axial alignment with longitudinal axis "X." The engagement of drive ring 2160 and manipulation knob 2170 is accomplished through the coupling of a pair of diametrically opposed radially outwardly extending engagement tabs 2168*a*, 2168*b* (2168*b* not shown) on drive ring 2160 with a pair of corresponding diametrically opposed interior recess 2172*a*, 2172*b* formed in the interior cavity of the manipulation knob 2170. Alternative structures may be provided to enable ready manipulation of drive ring 2160.

Referring again to FIGS. 20 and 21, a flange 2180 projects radially outwardly from the lower body portion 2114*b* of cannula housing 2144 to provide leverage to the surgeon when the manipulation knob 2170 is rotated.

It is also contemplated that the valve 2120 may be field replaceable. For example, if the surgical access device 2100 is provided with a valve 2120 having a 5 mm lumen and a 10 mm lumen, the physician would be able to substitute a valve 2120 having a 10 mm lumen and a 12 mm lumen. Other combinations of lumen sizes are contemplated and may be provided as part of a surgical kit.

While this particular embodiment is shown having seals 2132, 2142 disposed within lumen 2130, 2140, it should be recognized that, in other embodiments, the lumens 2130, 2140 may be devoid of seals, in which case one or more instrument (e.g., septum) and/or zero-closure (e.g., duckbill, flapper) seals may be provided elsewhere in the housing. In such an arrangement, the provision of different sized lumens 2130, 2140 may still provide sealing advantages as compared to conventional valve arrangements, e.g., by preventing instruments having varying diameters from being over-angulated by a user. For example, when a relatively small instrument is placed into a relatively large lumen, the relatively small instrument may be over-angulated relative to the wall of the lumen, thereby increasing the likelihood that the instrument will cause an instrument and/or zero-closure seal located elsewhere in the housing to experience "cat-eyeing" (e.g., "cat-eyeing" refers to a loss of sealing pressure due to small spaces that can form between a seal and the outer diameter of an instrument). By providing multiple lumen having different diameters, a user may select a lumen that is dimensionally appropriate for the instrument to be used, thereby reducing the likelihood that the instrument will be over-angulated relative to the walls of the lumen and reducing the likelihood that the instrument will cause an instrument and/or zero-closure seal located elsewhere in the housing to experience "cat-eyeing." Of course, such a benefit, e.g., the reduction of a likelihood of over-angulating and "cat-eyeing,"

may also be provided by embodiments of the present invention in which the seals 2132, 2142 are disposed within the lumen 2130, 2140.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

What is claimed is:

1. A valve system comprising:
    a valve housing having an upper body portion and a lower body portion, the upper and lower body portions being separable and defining an internal chamber and a central axis, the valve housing having axially aligned inlet and outlet ports formed in the upper and lower body portions, respectively;
    a first spherical valve member selectively positionable within the internal chamber of the valve housing, the first spherical valve member movable in the internal chamber between first and second positions, the first spherical valve member defining first and second bores that extend through the first spherical valve member, the first bore defining a first longitudinal axis and the second bore defining a second longitudinal axis offset relative to the first longitudinal axis, the first bore supporting a first seal and the second bore supporting a second seal, the first seal extending across the first bore and configured to sealingly engage a first surgical instrument having a first instrument diameter, the second seal extending across the second bore and configured to sealingly engage a second surgical instrument having a second instrument diameter that is different from the first instrument diameter; and
    a second spherical valve member selectively positionable within the internal chamber of the valve housing to replace the first spherical valve member.

2. The valve system as recited in claim 1, wherein the first bore defines a first diameter and the second bore defines a second diameter, the first diameter being different from the second diameter.

3. The valve system as recited in claim 1, wherein alignment of the first and second bores of the first spherical valve member with the inlet and outlet ports of the valve housing enables each one of the first and second bores to receive a surgical instrument.

4. The valve system as recited in claim 1, wherein the first spherical valve member is mounted for movement to a third position wherein the first and second bores of the first spherical valve member are both axially misaligned with the inlet and outlet ports of the valve housing.

5. The valve system as recited in claim 1, wherein the first spherical valve member is mounted for rotation within the internal chamber about an axis extending perpendicular to the central axis defined by the upper and lower body portion of the valve housing.

6. The valve system as recited in claim 1, wherein the valve housing is configured for connection to a cannula tube.

7. The valve system as recited in claim 1, further including a rotation mechanism configured to facilitate axial rotation of the lower body portion of the valve housing relative to the upper body portion of the valve housing.

8. The valve system as recited in claim 7, wherein the first spherical valve member moves between the first position and the second position when the upper body portion of the housing is rotated about the central axis between about 57 degrees and about 77 degrees with respect to the lower body portion.

9. The valve system of claim 1, wherein the second spherical valve defines at least two bores, wherein at least one of the at least two bores of the second spherical valve is dimensioned differently than at least one of the first and second bores of the first spherical valve.

10. A surgical system comprising:
    a valve housing having an upper body portion and a lower body portion, the upper and lower body portions being separable and defining an internal chamber and a central axis, the valve housing having axially aligned inlet and outlet ports formed in the upper and lower body portions, respectively;
    an elongated cannula sleeve coupled to the valve housing and defining an elongated passageway extending therethrough, the elongated cannula sleeve defining a long axis aligned with the inlet and outlet ports of the valve housing;
    a first spherical valve member selectively positionable within the internal chamber of the valve housing, the first spherical valve member movable in the internal chamber between first and second positions, the first spherical valve member defining first and second bores that extend through the first spherical valve member, the first bore defining a first longitudinal axis and the second bore defining a second longitudinal axis offset relative to the first longitudinal axis, the first bore supporting a first seal and the second bore supporting a second seal, the first seal extending across the first bore and configured to sealingly engage a first surgical instrument having a first instrument diameter, the second seal extending across the second bore and configured to sealingly engage a second surgical instrument having a second instrument diameter that is different from the first instrument diameter; and
    a second spherical valve member selectively positionable within the internal chamber of the valve housing to replace the first spherical valve member.

11. The surgical system as recited in claim 10, wherein the first bore defines a first diameter and the second bore defines a second diameter, the first diameter being different from the second diameter.

12. The surgical system as recited in claim 10, wherein alignment of the first and second bores of the first spherical valve member with the inlet and outlet ports of the valve housing enables each one of the first and second bores to receive a surgical instrument.

13. The surgical system as recited in claim 10, wherein the first spherical valve member is mounted within the internal chamber of the valve housing for movement to a third position wherein the first and second bores of the first spherical valve member are both axially misaligned with the inlet and outlet ports of the valve housing.

14. The surgical system as recited in claim 10, wherein the first spherical valve member is mounted for rotation within the internal chamber about an axis extending perpendicular to the central axis defined by the upper and lower body portion of the valve housing.

15. The surgical system as recited in claim 10, further including a rotation mechanism configured to facilitate axial rotation of the lower body portion of the valve housing relative to the upper body portion of the valve housing.

16. The surgical system as recited in claim 15, wherein the first spherical valve member moves between the first position and the second position when the upper body portion of the housing is rotated about the central axis between about 57 degrees and about 77 degrees with respect to the lower body portion.

17. The surgical system of claim 10, wherein the second spherical valve defines at least two bores, wherein at least one of the at least two bores of the second spherical valve is dimensioned differently than at least one of the first and second bores of the first spherical valve.

18. A valve system comprising:
a valve housing defining an internal chamber and having axially aligned inlet and outlet ports;
a first spherical valve member seated within the internal chamber of the valve housing and defining first and second bores that extend through the first spherical valve member, the first bore defining a first longitudinal axis and the second bore defining a second longitudinal axis offset relative to the first longitudinal axis, the first bore supporting a first seal and the second bore supporting a second seal, the first spherical valve member movable between a first position wherein the first bore of the first spherical valve member is axially aligned with the inlet and outlet ports of the valve housing and the second bore of the first spherical valve member is axially misaligned with the inlet and outlet ports of the valve housing, and a second position wherein the second bore of the first spherical valve member is axially aligned with the inlet and outlet ports of the valve housing and the first bore of the first spherical valve member is axially misaligned with the inlet and outlet ports of the valve housing, wherein the first spherical valve member is mounted for axial rotation within the internal chamber about an axis extending perpendicular to the axially aligned inlet and outlet ports of the valve housing;
a camming mechanism operatively associated with the valve housing and the first spherical valve member for moving the first spherical valve member between the first position and the second position, the camming mechanism including cam surfaces formed on an exterior surface of the first spherical valve member and a cam pin mounted for movement relative to the cam surfaces of the first spherical valve member, wherein the cam surfaces formed on the exterior surface of the first spherical valve member are defined by a pair of cam lobes oriented at angles to one another with respect to an axis of rotation of the first spherical valve member; and
a second spherical valve member selectively positionable within the internal chamber of the valve housing to replace the first spherical valve member.

* * * * *